(12) United States Patent
Spencer

(10) Patent No.: US 8,552,063 B2
(45) Date of Patent: Oct. 8, 2013

(54) COMPOSITION FOR ACCELERATED PRODUCTION OF COLLAGEN

(75) Inventor: Clifford Spencer, Lincolnshire (GB)

(73) Assignee: E.S.L.I. Limited, Tortola (VG)

( * ) Notice: Subject to any disclaimer, the term of this patent is extended or adjusted under 35 U.S.C. 154(b) by 166 days.

(21) Appl. No.: 13/056,736

(22) PCT Filed: Jul. 31, 2009

(86) PCT No.: PCT/GB2009/001891
§ 371 (c)(1),
(2), (4) Date: Jan. 31, 2011

(87) PCT Pub. No.: WO2010/013015
PCT Pub. Date: Feb. 4, 2010

(65) Prior Publication Data
US 2011/0130459 A1    Jun. 2, 2011

(30) Foreign Application Priority Data

Aug. 1, 2008 (GB) .................................. 0814105.3

(51) Int. Cl.
*A61K 31/202* (2006.01)
(52) U.S. Cl.
USPC ........................................................ 514/560
(58) Field of Classification Search
None
See application file for complete search history.

(56) References Cited

U.S. PATENT DOCUMENTS

| | | | |
|---|---|---|---|
| 6,340,485 B1 * | 1/2002 | Coupland et al. | 424/776 |
| 2007/0004678 A1 * | 1/2007 | Kohn et al. | 514/78 |
| 2007/0280898 A1 | 12/2007 | Riddle | |
| 2008/0045594 A1 * | 2/2008 | Piccirilli et al. | 514/558 |

FOREIGN PATENT DOCUMENTS

| | | |
|---|---|---|
| RO | 118 256 | 4/2003 |
| WO | 95/31176 | 11/1995 |
| WO | 97/46220 | 12/1997 |
| WO | 02/092073 | 11/2002 |
| WO | 03/105606 | 12/2003 |
| WO | 2005/056030 | 6/2005 |
| WO | 2007/004229 | 1/2007 |

OTHER PUBLICATIONS

International Search Report for corresponding patent application No. PCT/GB2009/001891 dated Jan. 10, 2011.
Database WPI, Week 200357, Thomson Scientific, London. GB; AN 2003-604691, XP002607331, & R0118 256 B(Farmec SA) Apr. 30, 2003. Abstract.

* cited by examiner

*Primary Examiner* — Blessing Fubara
*Assistant Examiner* — Jennifer Berrios
(74) *Attorney, Agent, or Firm* — Renner, Otto, Boisselle & Sklar, LLP

(57) ABSTRACT

Here the inventors provide a composition for topical application to the skin of animal comprising stearidonic acid in combination with one or octadecatrienoic acids (CODTAs). Preferably the composition comprises *echium* oil as a source of the stearidonic acid, and a plant lipid as a source of octadecatrienoic acid, such as borage oil (*Borago officinalis*), wheat germ oil (*Triticum vulgare*) rosehip oil (refined; *Rosa mosqueta*), jacaranda oil (*Jacandra mimosi folia*), and/or calendula oil (*Calendula officinalis*). The composition of the invention increases collagen I secretion and thus has particular utility for promoting collagen production in skin.

8 Claims, 28 Drawing Sheets

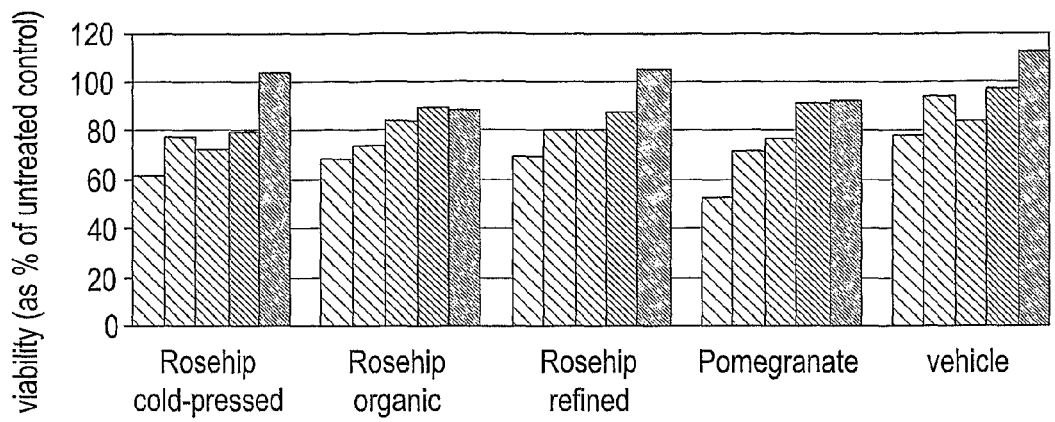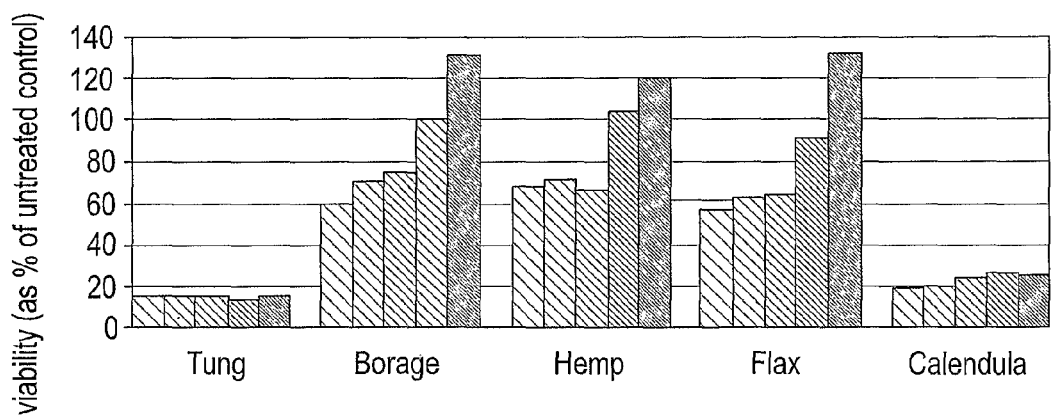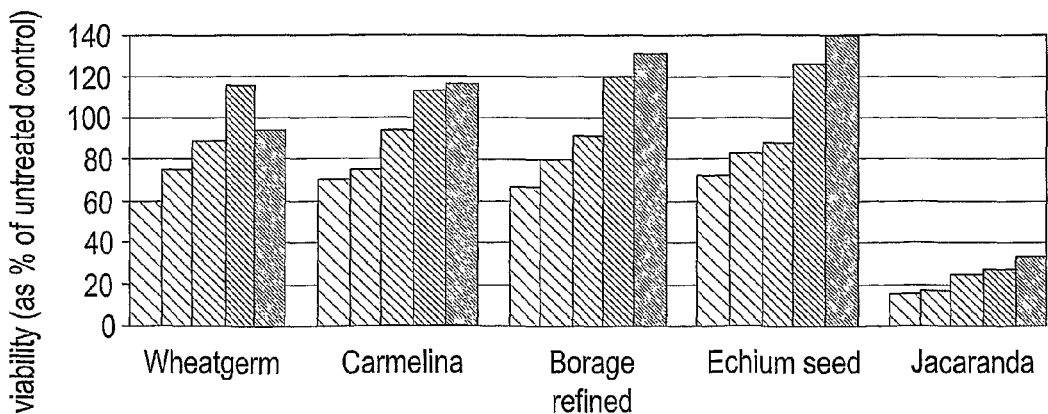
Figure 2

Figure 4

| Test oil name | Epistem reference | pre-dilution | tolerated volume (μl) | required final test oil dilution |
|---|---|---|---|---|
| Echium Oil | epi63 | 1/10 | 10 | 0.01 |
| Rosehip - cold pressed | epi27 | 1/10 | 1 | 0.001 |
| Rosehip - organic | epi28 | 1/100 | 6 | 0.0006 |
| Rosehip - refined | epi29 | 1/10 | 3 | 0.003 |
| Pomegranate | epi30 | 1/10 | 3 | 0.003 |
| Tung | epi31 | 1/100 | 1 | 0.001 |
| Borage | epi35 | 1/10 | 3 | 0.003 |
| Hemp | epi36 | 1/10 | 3 | 0.003 |
| Flax | epi37 | 1/10 | 3 | 0.003 |
| Wheatgerm | epi38 | 1/10 | 6 | 0.006 |
| Carmelina | epi39 | 1/10 | 6 | 0.006 |
| Borage - refined | epi40 | 1/10 | 6 | 0.006 |
| Echium seed | epi41 | 1/10 | 6 | 0.006 |
| Jacaranda | epi60 | 1/100 | 3 | 0.0003 |
| Calendula | epi61 | 1/100 | 3 | 0.0003 |

| Epistem reference | To make 1000μl of oil mix | | | | | | |
|---|---|---|---|---|---|---|---|
| | Echium oil volume(μl) | Test oil volume(μl) | Total oil volume(μl) | diluent volume(μl) | total volume(μl) | Test oil dilution | Echium oil dilution |
| epi63 | 100 | 0 | 100 | 900 | 1000 | 0.000 | 0.100 |
| epi27 | 30 | 10 | 40 | 960 | 1000 | 0.010 | 0.030 |
| epi28 | 18 | 6 | 24 | 976 | 1000 | 0.006 | 0.018 |
| epi29 | 100 | 33.3 | 133.3 | 866.7 | 1000 | 0.033 | 0.100 |
| epi30 | 100 | 33.3 | 133.3 | 866.7 | 1000 | 0.033 | 0.100 |
| epi31 | 30 | 10 | 40 | 960 | 1000 | 0.010 | 0.030 |
| epi35 | 100 | 33.3 | 133.3 | 866.7 | 1000 | 0.033 | 0.100 |
| epi36 | 100 | 33.3 | 133.3 | 866.7 | 1000 | 0.033 | 0.100 |
| epi37 | 100 | 33.3 | 133.3 | 866.7 | 1000 | 0.033 | 0.100 |
| epi38 | 100 | 33.3 | 133.3 | 866.7 | 1000 | 0.033 | 0.100 |
| epi39 | 100 | 33.3 | 133.3 | 866.7 | 1000 | 0.033 | 0.100 |
| epi40 | 100 | 33.3 | 133.3 | 866.7 | 1000 | 0.033 | 0.100 |
| epi41 | 100 | 33.3 | 133.3 | 866.7 | 1000 | 0.033 | 0.100 |
| epi60 | 9 | 3 | 12 | 988 | 1000 | 0.003 | 0.009 |
| epi61 | 9 | 3 | 12 | 988 | 1000 | 0.003 | 0.009 |

| Epistem reference | Within cell culture wells | | |
|---|---|---|---|
| | Final test oil dilution | Final echium oil dilution | Echium oil:Test oil ratio |
| epi63 | 0.0000 | 0.01 | n/a |
| epi27 | 0.0010 | 0.003 | 3:1 |
| epi28 | 0.0006 | 0.0016 | 3:1 |
| epi29 | 0.0033 | 0.01 | 3:1 |
| epi30 | 0.0033 | 0.01 | 3:1 |
| epi31 | 0.0010 | 0.003 | 3:1 |
| epi35 | 0.0033 | 0.01 | 3:1 |
| epi36 | 0.0033 | 0.01 | 3:1 |
| epi37 | 0.0033 | 0.01 | 3:1 |
| epi38 | 0.0033 | 0.01 | 3:1 |
| epi39 | 0.0033 | 0.01 | 3:1 |
| epi40 | 0.0033 | 0.01 | 3:1 |
| epi41 | 0.0033 | 0.01 | 3:1 |
| epi60 | 0.0003 | 0.0009 | 3:1 |
| epi61 | 0.0003 | 0.0009 | 3:1 |

Plate 1:

|   | 1 | 2 | 3 | 4 | 5 | 6 | 7 | 8 | 9 | 10 | 11 | 12 |
|---|---|---|---|---|---|---|---|---|---|---|---|---|
| A | x | neat echium oil Epi63 | | | | x | ?? | 1/10 Echium oil epi63-in medium | | | | |
| B | x | 10 | 8 | 6 | 3 | x | | 10 | 8 | 6 | 3 | 1 |
| C | x | | | | | x | | | | | | |
| D | x | 1/100 Echium oil Epi63-in medium | | | | x | | medium only | | | | |
| E | x | 10 | 8 | 6 | 3 | x | | 10 | 8 | 6 | 3 | 1 |
| F | x | | | | | x | | | | | | |
| G | x | 2mM BSA/1.8% DMBO in medium | | | | | 2mM BSA in medium | | | | | x |
| H | x | x | x | x | x | x | x | x | x | x | x | x |

|   | 1 | 2 | 3 | 4 | 5 | 6 | 7 | 8 | 9 | 10 | 11 | 12 |
|---|---|---|---|---|---|---|---|---|---|---|---|---|
| A | x | 200 | 250 | 242 | 288 | x | 1382 | 1626 | 1738 | 1753 | 1712 | 1713 |
| B | x | 174 | 201 | 229 | 191 | x | 1398 | 1793 | 1688 | 1797 | 1586 | 1604 |
| C | x | 175 | 197 | 207 | 188 | x | 1552 | 1221 | 1765 | 1627 | 1516 | 1509 |
| D | x | 1364 | 1444 | 1529 | 1636 | x | 1535 | 1530 | 1707 | 1390 | 1401 | 1369 |
| E | x | 1227 | 1079 | 1172 | 1361 | x | 1188 | 1365 | 1467 | 1473 | 1377 | 1304 |
| F | x | 1286 | 1071 | 890 | 1487 | x | 1439 | 1150 | 1258 | 1333 | 1432 | 1377 |
| G | x | 1738 | 1269 | 924 | 1429 | 1452 | 1380 | 1501 | 1579 | 1355 | 1380 | x |
| H | x | x | x | x | x | x | x | x | x | x | x | x |

Plate 2:

|   | 1 | 2 | 3 | 4 | 5 | 6 | 7 | 8 | 9 | 10 | 11 | 12 |
|---|---|---|---|---|---|---|---|---|---|---|---|---|
| A | x | 1/10 Echium oil Epi633-In 2mM BSA | | | | | 1/10 Echium oil Epi633-In 2mM BSA/ 1.8% DMBO | | | | | x |
| B | x | 10 | 8 | 6 | 3 | 1 | 10 | 8 | 6 | 3 | 1 | x |
| C | x | | | | | | | | | | | x |
| D | x | 1/100 Echium oil Epi633-In 2mM BSA | | | | | 1/100 Echium oil Epi633-In 2mM BSA/ 1.8% DMBO | | | | | x |
| E | x | 10 | 8 | 6 | 3 | 1 | 10 | 8 | 6 | 3 | 1 | x |
| F | x | | | | | | | | | | | x |
| G | x | 2mM BSA in medium | | | | | 2mM BSA/1.8% DMBO in medium | | | | | x |
| H | x | 10 | 8 | 6 | 3 | 1 | 10 | 8 | 6 | 3 | 1 | x |

|   | 1 | 2 | 3 | 4 | 5 | 6 | 7 | 8 | 9 | 10 | 11 | 12 |
|---|---|---|---|---|---|---|---|---|---|---|---|---|
| A | x | 1053 | 1243 | 1580 | 1377 | 501 | 1814 | 1793 | 1391 | 1601 | 1656 | x |
| B | x | 1136 | 928 | 1434 | 1473 | 1188 | 1714 | 1696 | 1231 | 1787 | 1365 | x |
| C | x | 308 | 1029 | 1128 | 1339 | 1281 | 1539 | 1674 | 1592 | 1557 | 1438 | x |
| D | x | 1326 | 1209 | 1201 | 1384 | 1187 | 1612 | 1484 | 1277 | 1544 | 1394 | x |
| E | x | 315 | 568 | 916 | 1420 | 1234 | 1404 | 1395 | 1129 | 1553 | 1396 | x |
| F | x | 335 | 592 | 270 | 1387 | 1165 | 1400 | 1489 | 1218 | 1565 | 1336 | x |
| G | x | 1141 | 1328 | 1343 | 1351 | 1334 | 1569 | 1406 | 1337 | 1515 | 1466 | x |
| H | x | 1367 | 1397 | 1429 | 1443 | 1386 | 1369 | 1650 | 1270 | 1735 | 1481 | x |

Figure 6

| neat Echium oil epi63 | | | |
|---|---|---|---|
| 10 | 8 | 6 | 3 |
| 13.99 | 17.49 | 16.93 | 20.15 |
| 12.17 | 14.06 | 16.02 | 13.36 |
| 12.24 | 13.78 | 14.48 | 13.15 |
| 12.80 | 15.11 | 15.81 | 15.55 |

| 1/10 Echium oil epi63 - In medium | | | | |
|---|---|---|---|---|
| 10 | 8 | 6 | 3 | 1 |
| 113.74 | 121.57 | 122.62 | 119.76 | 119.83 |
| 125.42 | 118.08 | 125.70 | 110.94 | 112.20 |
| 85.41 | 123.46 | 113.81 | 106.05 | 105.56 |
| 108.19 | 121.04 | 120.71 | 112.25 | 112.53 |

| 1/100 Echium oil epi63 - In medium | | | |
|---|---|---|---|
| 10 | 8 | 6 | 3 |
| 95.41 | 101.01 | 106.96 | 114.44 |
| 85.83 | 75.48 | 81.98 | 95.20 |
| 89.95 | 74.92 | 62.26 | 104.02 |
| 90.40 | 83.80 | 83.73 | 104.55 |

| medium only | | | | |
|---|---|---|---|---|
| 10 | 8 | 6 | 3 | 1 |
| 107.03 | 119.41 | 97.23 | 98.00 | 95.76 |
| 95.48 | 102.62 | 103.04 | 96.32 | 91.22 |
| 80.44 | 88.00 | 93.24 | 100.17 | 96.32 |
| 94.32 | 103.34 | 97.84 | 98.16 | 94.43 |

| 1/10 Echium oil epi63 - In 2mM BSA | | | | |
|---|---|---|---|---|
| 10 | 8 | 6 | 3 | 1 |
| 73.66 | 86.95 | 110.52 | 96.32 | |
| 79.45 | 64.91 | 100.31 | 103.04 | 83.10 |
| | 71.98 | 78.90 | 93.66 | 89.61 |
| 76.56 | 74.61 | 96.58 | 97.67 | 86.35 |

| 1/10 Echium oil epi63 - In 2mM BSA/1.8% DMBO | | | | |
|---|---|---|---|---|
| 10 | 8 | 6 | 3 | 1 |
| 126.89 | 125.42 | 97.30 | 111.99 | 115.84 |
| 119.90 | 118.64 | 86.11 | 125.00 | 95.48 |
| 107.65 | 117.10 | 111.36 | 108.91 | 100.59 |
| 118.15 | 120.39 | 98.26 | 115.30 | 103.97 |

| 1/100 Echium oil epi63 - In 2mM BSA | | | | |
|---|---|---|---|---|
| 10 | 8 | 6 | 3 | 1 |
| 92.76 | 84.57 | 84.01 | 96.81 | 83.03 |
| | | 64.08 | 99.33 | 86.32 |
| | | 97.02 | | 81.49 |
| 92.76 | 84.57 | 74.04 | 97.72 | 83.61 |

| 1/100 Echium oil epi63 - In 2mM BSA/1.8% DMBO | | | | |
|---|---|---|---|---|
| 10 | 8 | 6 | 3 | 1 |
| 112.76 | 103.81 | 89.33 | 108.00 | 97.51 |
| 98.21 | 97.58 | 78.97 | 108.63 | 97.55 |
| 97.93 | 104.16 | 85.20 | 109.47 | 93.45 |
| 102.97 | 101.85 | 84.50 | 108.70 | 96.21 |

| 2mM BSA In medium | | | | |
|---|---|---|---|---|
| 10 | 8 | 6 | 3 | 1 |
| 79.81 | 92.89 | 93.94 | 94.50 | 93.31 |
| 95.62 | 97.72 | 99.96 | 100.94 | 96.96 |
| 96.53 | 105.00 | 110.45 | 94.78 | 95.53 |
| 90.66 | 98.54 | 101.45 | 96.74 | 95.60 |

| 2mM BSA/1.8% DMBO in medium | | | | |
|---|---|---|---|---|
| 10 | 8 | 6 | 3 | 1 |
| 109.75 | 98.35 | 93.52 | 105.98 | 102.55 |
| 95.76 | 115.42 | 88.84 | 121.37 | 103.60 |
| 121.57 | 88.77 | 64.63 | 99.96 | 101.57 |
| 109.03 | 100.86 | 82.33 | 109.10 | 102.57 |

Figure 7

Figure 8: page 1

Plate 1:

|   | 1 | 2 | 3 | 4 | 5 | 6 | 7 | 8 | 9 | 10 | 11 | 12 |
|---|---|---|---|---|---|---|---|---|---|---|---|---|
| A |   | Epi27 |   |   |   |   | Epi28 |   |   |   | UNTREATED | |
| B | 10 | 8 | 6 | 3 | 1 | 10 | 8 | 6 | 3 | 1 | | |
| C |   |   |   |   |   |   |   |   |   |   |   |   |
| D |   | Epi29 |   |   |   |   | Epi30 |   |   |   | X | X |
| E | 10 | 8 | 6 | 3 | 1 | 10 | 8 | 6 | 3 | 1 | X | X |
| F |   |   |   |   |   |   |   |   |   |   | X | X |
| G |   | Vehicle |   |   |   |   | Vehicle |   |   |   | X | X |
| H |   | Vehicle |   |   |   |   |   |   |   |   | X | X |

|   | 1 | 2 | 3 | 4 | 5 | 6 | 7 | 8 | 9 | 10 | 11 | 12 |
|---|---|---|---|---|---|---|---|---|---|---|---|---|
| A | 1293 | 1368 | 1149 | 1200 | 1744 | 1114 | 1405 | 1629 | 1608 | 1152 | 1385 | 1523 |
| B | 1026 | 1366 | 1327 | 1709 | 1913 | 1214 | 1144 | 1494 | 1655 | 1798 | 1853 | 2037 |
| C | 971 | 1357 | 1388 | 1266 | 1837 | 1301 | 1370 | 1334 | 1479 | 1717 | 1920 | 1867 |
| D | 1262 | 1507 | 1497 | 1588 | 1907 | 1041 | 1356 | 1360 | 1285 | 1776 | X | X |
| E | 1228 | 1287 | 1433 | 1540 | 1831 | 898 | 1136 | 1458 | 1754 | 1561 | X | X |
| F | 1185 | 1421 | 1319 | 1527 | 1892 | 883 | 1327 | 1263 | 1778 | 1544 | X | X |
| G | 1342 | 1635 | 1615 | 1915 | 2382 | 1429 | 1540 | 1332 | 1511 | 1823 | X | X |
| H | X | 1829 | 1496 | 1737 | 1779 | 1964 | X | X | X | X | X | X |

Plate 2:

|   | 1 | 2 | 3 | 4 | 5 | 6 | 7 | 8 | 9 | 10 | 11 | 12 |
|---|---|---|---|---|---|---|---|---|---|---|---|---|
| A |   | Epi31 |   |   |   |   | Epi35 |   |   |   | X | X |
| B | 10 | 8 | 6 | 3 | 1 | 10 | 8 | 6 | 3 | 1 | X | X |
| C |   |   |   |   |   |   |   |   |   |   | X | X |
| D |   | Epi36 |   |   |   |   | Epi37 |   |   |   | X | X |
| E | 10 | 8 | 6 | 3 | 1 | 10 | 8 | 6 | 3 | 1 | X | X |
| F |   |   |   |   |   |   |   |   |   |   | X | X |
| G | X | X | X | X | X | X | X | X | X | X | X | X |
| H | X | X | X | X | X | X | X | X | X | X | X | X |

|   | 1 | 2 | 3 | 4 | 5 | 6 | 7 | 8 | 9 | 10 | 11 | 12 |
|---|---|---|---|---|---|---|---|---|---|---|---|---|
| A | 249 | 227 | 247 | 223 | 231 | 1023 | 1313 | 1206 | 1777 | 2017 | X | X |
| B | 251 | 263 | 237 | 242 | 231 | 1027 | 1234 | 1400 | 1711 | 2539 | X | X |
| C | 259 | 253 | 264 | 232 | 258 | 1058 | 1165 | 1359 | 1803 | 2412 | X | X |
| D | 1279 | 1119 | 1318 | 2133 | 2451 | 1013 | 1109 | 1202 | 1103 | 2237 | X | X |
| E | 1198 | 1302 | 1012 | 1855 | 1517 | 1019 | 935 | 1144 | 2152 | 2460 | X | X |
| F | 1100 | 1374 | 1181 | 1506 | 2458 | 961 | 1218 | 1036 | 1578 | 2313 | X | X |
| G | X | X | X | X | X | X | X | X | X | X | X | X |
| H | X | X | X | X | X | X | X | X | X | X | X | X |

Figure 8: page 2

Plate 3:

|   | 1 | 2 | 3 | 4 | 5 | 6 | 7 | 8 | 9 | 10 | 11 | 12 |
|---|---|---|---|---|---|---|---|---|---|----|----|----|
| A |   | Epi38 |   |   |   |   | Epi39 |   |   |   | X | X |
| B | 10 | 8 | 6 | 3 | 1 | 10 | 8 | 6 | 3 | 1 | X | X |
| C |   |   |   |   |   |   |   |   |   |   | X | X |
| D |   | Epi40 |   |   |   |   | Epi41 |   |   |   | X | X |
| E | 10 | 8 | 6 | 3 | 1 | 10 | 8 | 6 | 3 | 1 | X | X |
| F |   |   |   |   |   |   |   |   |   |   | X | X |
| G | X | X | X | X | X | X | X | X | X | X | X | X |
| H | X | X | X | X | X | X | X | X | X | X | X | X |

|   | 1 | 2 | 3 | 4 | 5 | 6 | 7 | 8 | 9 | 10 | 11 | 12 |
|---|---|---|---|---|---|---|---|---|---|----|----|----|
| A | 1299 | 1301 | 1694 | 1703 | 1255 | 1143 | 1376 | 1660 | 1968 | 2030 | X | X |
| B | 1102 | 1386 | 1684 | 1861 | 2197 | 1225 | 1271 | 1687 | 2146 | 2204 | X | X |
| C | 779 | 1302 | 1351 | 2553 | 1578 | 1314 | 1358 | 1658 | 1814 | 1955 | X | X |
| D | 1070 | 1434 | 1539 | 2078 | 2437 | 1375 | 1530 | 1585 | 2261 | 2332 | X | X |
| E | 1283 | 1374 | 1570 | 2189 | 2458 | 1266 | 1447 | 1432 | 2080 | 2565 | X | X |
| F | 1155 | 1402 | 1721 | 2063 | 2024 | 1198 | 1417 | 1642 | 2306 | 2508 | X | X |
| G | X | X | X | X | X | X | X | X | X | X | X | X |
| H | X | X | X | X | X | X | X | X | X | X | X | X |

Plate 4:

|   | 1 | 2 | 3 | 4 | 5 | 6 | 7 | 8 | 9 | 10 | 11 | 12 |
|---|---|---|---|---|---|---|---|---|---|----|----|----|
| A |   | Epi50 |   |   |   |   | Epi51 |   |   |   | X | X |
| B | 10 | 8 | 6 | 3 | 1 | 10 | 8 | 6 | 3 | 1 | X | X |
| C |   |   |   |   |   |   |   |   |   |   | X | X |
| D | X | X | X | X | X | X | X | X | X | X | X | X |
| E | X | X | X | X | X | X | X | X | X | X | X | X |
| F | X | X | X | X | X | X | X | X | X | X | X | X |
| G | X | X | X | X | X | X | X | X | X | X | X | X |
| H | X | X | X | X | X | X | X | X | X | X | X | X |

|   | 1 | 2 | 3 | 4 | 5 | 6 | 7 | 8 | 9 | 10 | 11 | 12 |
|---|---|---|---|---|---|---|---|---|---|----|----|----|
| A | 336 | 367 | 464 | 532 | 671 | 382 | 424 | 486 | 463 | 389 | X | X |
| B | 313 | 372 | 551 | 607 | 833 | 377 | 444 | 534 | 617 | 805 | X | X |
| C | 301 | 340 | 548 | 531 | 591 | 432 | 387 | 500 | 666 | 357 | X | X |
| D | X | X | X | X | X | X | X | X | X | X | X | X |
| E | X | X | X | X | X | X | X | X | X | X | X | X |
| F | X | X | X | X | X | X | X | X | X | X | X | X |
| G | X | X | X | X | X | X | X | X | X | X | X | X |
| H | X | X | X | X | X | X | X | X | X | X | X | X |

Figure 9

| Epi27 | | | | |
|---|---|---|---|---|
| 10 | 8 | 6 | 3 | 1 |
| 73.29 | 77.54 | 65.13 | 68.02 | 98.86 |
| 58.16 | 77.43 | 75.22 | 96.87 | 108.44 |
| 55.04 | 76.92 | 78.68 | 71.76 | 104.13 |
| 62.16 | 77.30 | 73.01 | 78.89 | 103.81 |

| Epi28 | | | | |
|---|---|---|---|---|
| 10 | 8 | 6 | 3 | 1 |
| 63.15 | 79.64 | 92.34 | 91.15 | 65.30 |
| 68.81 | 64.85 | 84.69 | 93.81 | 101.92 |
| 73.75 | 77.66 | 75.62 | 83.84 | 97.33 |
| 68.57 | 74.05 | 84.21 | 89.60 | 88.18 |

| Epi29 | | | | |
|---|---|---|---|---|
| 10 | 8 | 6 | 3 | 1 |
| 71.54 | 85.42 | 84.86 | 90.01 | 108.10 |
| 69.61 | 72.95 | 81.23 | 87.29 | 103.79 |
| 67.17 | 80.55 | 74.77 | 86.56 | 107.25 |
| 69.44 | 79.64 | 80.28 | 87.95 | 106.38 |

| Epi30 | | | | |
|---|---|---|---|---|
| 10 | 8 | 6 | 3 | 1 |
| 59.01 | 76.86 | 77.09 | 72.84 | 100.67 |
| 50.90 | 64.39 | 82.65 | 99.42 | 88.48 |
| 50.05 | 75.22 | 71.59 | 100.78 | 87.52 |
| 53.32 | 72.16 | 77.11 | 91.02 | 92.22 |

| Vehicle | | | | |
|---|---|---|---|---|
| 10 | 8 | 6 | 3 | 1 |
| 76.07 | 92.68 | 91.54 | 108.55 | 135.02 |
| 103.68 | 84.80 | 98.46 | 100.84 | 111.33 |
| 81.00 | 87.29 | 75.50 | 85.65 | 103.33 |
| 86.92 | 88.26 | 88.50 | 98.35 | 116.56 |

| Epi31 | | | | |
|---|---|---|---|---|
| 10 | 8 | 6 | 3 | 1 |
| 14.11 | 12.87 | 14.00 | 12.64 | 13.09 |
| 14.23 | 14.91 | 13.43 | 13.72 | 13.09 |
| 14.68 | 14.34 | 14.96 | 13.15 | 14.62 |
| 14.34 | 14.04 | 14.13 | 13.17 | 13.60 |

| Epi35 | | | | |
|---|---|---|---|---|
| 10 | 8 | 6 | 3 | 1 |
| 57.99 | 74.43 | 68.36 | 100.73 | 114.33 |
| 58.21 | 69.95 | 79.35 | 96.99 | 143.92 |
| 59.97 | 66.04 | 77.03 | 102.20 | 136.72 |
| 58.72 | 70.14 | 74.92 | 99.97 | 131.66 |

| Epi36 | | | | |
|---|---|---|---|---|
| 10 | 8 | 6 | 3 | 1 |
| 72.50 | 63.43 | 74.71 | 120.91 | 138.93 |
| 67.91 | 73.80 | 57.36 | 105.15 | 85.99 |
| 62.35 | 77.88 | 66.94 | 86.37 | 139.33 |
| 67.59 | 71.71 | 66.34 | 103.81 | 121.42 |

| Epi37 | | | | |
|---|---|---|---|---|
| 10 | 8 | 6 | 3 | 1 |
| 57.42 | 62.86 | 68.13 | 62.52 | 126.80 |
| 57.76 | 53.00 | 64.85 | 121.98 | 139.44 |
| 54.47 | 69.04 | 58.72 | 89.45 | 131.11 |
| 56.55 | 61.63 | 63.90 | 91.32 | 132.45 |

| Epi38 | | | | |
|---|---|---|---|---|
| 10 | 8 | 6 | 3 | 1 |
| 73.63 | 73.75 | 96.02 | 96.53 | 71.14 |
| 62.47 | 78.56 | 95.46 | 105.49 | 124.53 |
| 44.16 | 73.80 | 76.58 | 144.71 | 89.45 |
| 60.09 | 75.37 | 89.35 | 115.58 | 95.04 |

| Epi39 | | | | |
|---|---|---|---|---|
| 10 | 8 | 6 | 3 | 1 |
| 64.79 | 78.00 | 94.10 | 111.55 | 115.07 |
| 69.44 | 72.05 | 95.63 | 121.64 | 124.93 |
| 74.48 | 76.98 | 93.98 | 102.82 | 110.82 |
| 69.57 | 75.67 | 94.57 | 112.01 | 116.94 |

| Epi40 | | | | |
|---|---|---|---|---|
| 10 | 8 | 6 | 3 | 1 |
| 60.65 | 81.28 | 87.24 | 117.79 | 138.14 |
| 72.73 | 77.88 | 88.99 | 124.08 | 139.33 |
| 65.53 | 79.47 | 97.55 | 116.94 | 114.73 |
| 66.30 | 79.55 | 91.26 | 119.60 | 130.73 |

| Epi41 | | | | |
|---|---|---|---|---|
| 10 | 8 | 6 | 3 | 1 |
| 77.94 | 86.73 | 89.84 | 128.16 | 132.19 |
| 71.76 | 82.02 | 81.17 | 117.90 | 145.39 |
| 67.91 | 80.32 | 93.08 | 130.71 | 142.16 |
| 72.54 | 83.02 | 88.03 | 125.59 | 139.91 |

| Epi60 | | | | |
|---|---|---|---|---|
| 10 | 8 | 6 | 3 | 1 |
| 16.17 | 17.67 | 22.34 | 25.61 | 32.30 |
| 15.07 | 17.91 | 26.52 | 29.22 | 40.10 |
| 14.49 | 16.37 | 26.38 | 25.56 | 28.45 |
| 15.24 | 17.31 | 25.08 | 26.80 | 33.62 |

| Epi61 | | | | |
|---|---|---|---|---|
| 10 | 8 | 6 | 3 | 1 |
| 18.39 | 20.41 | 23.40 | 22.29 | 18.73 |
| 18.15 | 21.37 | 25.71 | 29.70 | 38.75 |
| 20.80 | 18.63 | 24.07 | 32.06 | 17.19 |
| 19.11 | 20.14 | 24.39 | 28.02 | 24.89 |

Figure 10

Plate 1:

|   | 1 | 2 | 3 | 4 | 5 | 6 | 7 | 8 | 9 | 10 | 11 | 12 |
|---|---|---|---|---|---|---|---|---|---|----|----|----|
| A |   | Epi28 1/100 | | | | | Epi30 1/100 | | | | X | X |
| B | 10 | 8 | 6 | 3 | 1 | 10 | 8 | 6 | 3 | 1 | X | X |
| C |   |   |   |   |   |   |   |   |   |   | X | X |
| D |   | Epi38 1/10 | | | | | Epi31 1/100 | | | | X | X |
| E | 10 | 8 | 6 | 3 | 1 | 10 | 8 | 6 | 3 | 1 | X | X |
| F |   |   |   |   |   |   |   |   |   |   | X | X |
| G |   | Vehicle | | | | | Vehicle | | | | X | X |
| H | 10 | 8 | 6 | 3 | 1 |   | UNTREATED | | | | X | X |

|   | 1 | 2 | 3 | 4 | 5 | 6 | 7 | 8 | 9 | 10 | 11 | 12 |
|---|---|---|---|---|---|---|---|---|---|----|----|----|
| A | 801 | 972 | 1164 | 1102 | 1074 | 927 | 1029 | 979 | 615 | 1227 | X | X |
| B | 1110 | 1321 | 1420 | 1506 | 1535 | 1607 | 1376 | 1714 | 1207 | 1529 | X | X |
| C | 1165 | 1102 | 1349 | 1479 | 1487 | 1347 | 1395 | 1442 | 1603 | 1704 | X | X |
| D | 1205 | 1378 | 1236 | 1421 | 1353 | 181 | 205 | 190 | 166 | 1444 | X | X |
| E | 1192 | 1329 | 1312 | 1177 | 1270 | 197 | 199 | 206 | 209 | 1708 | X | X |
| F | 1201 | 1397 | 1325 | 1052 | 1236 | 200 | 206 | 198 | 201 | 1372 | X | X |
| G | 108 | 1366 | 1555 | 1340 | 1234 | 1608 | 1437 | 1402 | 1033 | 1612 | X | X |
| H | 102 | 999 | 1477 | 1029 | 934 | 1117 | 1014 | 1326 | 1161 | 1561 | X | X |

Plate 2:

|   | 1 | 2 | 3 | 4 | 5 | 6 | 7 | 8 | 9 | 10 | 11 | 12 |
|---|---|---|---|---|---|---|---|---|---|----|----|----|
| A |   | Epi31 1/1000 | | | | | Epi31 1/100 | | | | X | X |
| B | 10 | 8 | 6 | 3 | 1 | 10 | 8 | 6 | 3 | 1 | X | X |
| C |   |   |   |   |   |   |   |   |   |   | X | X |
| D |   | Epi30 1/100 | | | | | control untreated | | | | X | X |
| E | 10 | 8 | 6 | 3 | 1 |   |   |   |   |   | X | X |
| F |   |   |   |   |   |   |   |   |   |   | X | X |
| G | X | X | X | X | X | X | X | X | X | X | X | X |
| H | X | X | X | X | X | X | X | X | X | X | X | X |

|   | 1 | 2 | 3 | 4 | 5 | 6 | 7 | 8 | 9 | 10 | 11 | 12 |
|---|---|---|---|---|---|---|---|---|---|----|----|----|
| A | 1156 | 1055 | 1120 | 1061 | 1100 | 248 | 1313 | 280 | 1113 | 1116 | X | X |
| B | 1033 | 1168 | 980 | 1125 | 1084 | 252 | 1234 | 301 | 1053 | 901 | X | X |
| C | 978 | 1028 | 1083 | 1018 | 991 | 266 | 1165 | 391 | 917 | 1084 | X | X |
| D | 267 | 648 | 842 | 1095 | 853 | 817 | 1009 | 1009 | 1058 | 1070 | X | X |
| E | 283 | 829 | 896 | 1074 | 978 | 791 | 982 | 995 | 1074 | 1105 | X | X |
| F | 439 | 822 | 854 | 875 | 938 | 958 | 1021 | 1002 | 1130 | 1161 | X | X |
| G | X | X | X | X | X | X | X | X | X | X | X | X |
| H | X | X | X | X | X | X | X | X | X | X | X | X |

| | Epi28 1/100 | | | |
|---|---|---|---|---|
| 10 | 8 | 6 | 3 | 1 |
| 64.82 | 78.65 | 95.81 | 89.17 | 86.91 |
| 89.82 | 106.89 | 114.91 | 121.86 | 124.21 |
| 94.27 | 89.17 | 109.16 | 119.68 | 120.33 |
| 82.97 | 91.57 | 106.62 | 110.24 | 110.48 |

| | Epi30 1/100 | | | |
|---|---|---|---|---|
| 10 | 8 | 6 | 3 | 1 |
| 75.01 | 83.27 | 79.22 | 49.77 | 99.29 |
| 130.04 | 111.34 | 138.70 | 97.67 | 123.73 |
| 109.00 | 112.88 | 116.69 | 129.71 | 137.89 |
| 104.68 | 102.50 | 111.53 | 92.38 | 120.30 |

| | Epi38 1/100 | | | |
|---|---|---|---|---|
| 10 | 8 | 6 | 3 | 1 |
| 97.51 | 111.51 | 100.02 | 114.99 | 109.48 |
| 96.46 | 107.54 | 106.17 | 96.24 | 102.77 |
| 97.18 | 113.04 | 107.22 | 86.13 | 100.02 |
| 97.05 | 110.70 | 104.47 | 98.45 | 104.09 |

| | Epi31 1/100 | | | |
|---|---|---|---|---|
| 10 | 8 | 6 | 3 | 1 |
| 14.65 | 16.59 | 15.37 | 13.43 | 116.85 |
| 16.94 | 16.10 | 16.67 | 16.91 | 138.21 |
| 16.18 | 16.67 | 16.02 | 16.26 | 111.02 |
| 15.59 | 16.45 | 16.02 | 15.54 | 122.03 |

| | Vehicle | | | |
|---|---|---|---|---|
| 10 | 8 | 6 | 3 | 1 |
| | 110.54 | 125.83 | 108.43 | 99.85 |
| | 80.84 | 119.52 | 83.27 | 75.58 |
| 130.12 | 116.28 | 113.45 | 83.59 | 130.44 |
| 130.12 | 102.55 | 119.60 | 91.76 | 101.96 |

| | Epi31 1/1000 | | | |
|---|---|---|---|---|
| 10 | 8 | 6 | 3 | 1 |
| 114.21 | 104.24 | 110.66 | 104.83 | 108.68 |
| 102.06 | 115.40 | 96.83 | 111.15 | 107.10 |
| 96.63 | 101.57 | 107.00 | 100.58 | 97.91 |
| 104.30 | 107.07 | 104.83 | 105.52 | 104.56 |

| | Epi60 1/100 | | | |
|---|---|---|---|---|
| 10 | 8 | 6 | 3 | 1 |
| 24.50 | 27.66 | 38.43 | 109.97 | 110.26 |
| 25.89 | 29.74 | 61.26 | 104.04 | 89.02 |
| 26.28 | 38.63 | 70.05 | 90.60 | 107.10 |
| 25.56 | 32.01 | 56.58 | 101.53 | 102.13 |

| | Epi61 1/100 | | | |
|---|---|---|---|---|
| 10 | 8 | 6 | 3 | 1 |
| 26.38 | 64.02 | 83.19 | 108.19 | 84.28 |
| 27.96 | 81.91 | 88.53 | 103.25 | 96.63 |
| 43.37 | 81.21 | 84.38 | 86.45 | 92.68 |
| 32.57 | 75.71 | 85.36 | 99.30 | 91.19 |

Figure 11

|   | 1 | 2 | 3 | 4 | 5 | 6 | 7 | 8 | 9 | 10 | 11 | 12 |
|---|---|---|---|---|---|---|---|---|---|---|---|---|
| A | epi27 | epi28 | epi29 | epi30 | epi31 | epi35 | epi36 | epi37 | epi38 | epi39 | epi40 | epi41 |
| B | epi27 | epi28 | epi29 | epi30 | epi31 | epi35 | epi36 | epi37 | epi38 | epi39 | epi40 | epi41 |
| C | epi27 | epi28 | epi29 | epi30 | epi31 | epi35 | epi36 | epi37 | epi38 | epi39 | epi40 | epi41 |
| D | X | X | X | X | X | X | X | X | X | X | X | X |
| E | X | X | X | X | X | X | X | X | X | X | X | X |
| F | epi60 | epi61 | echium | vehicle | untreated | X | X | X | X | X | X | X |
| G | epi60 | epi61 | echium | vehicle | untreated | X | X | X | X | X | X | X |
| H | epi60 | epi61 | echium | vehicle | untreated | X | X | X | X | X | X | X |

|   | 1 | 2 | 3 | 4 | 5 | 6 | 7 | 8 | 9 | 10 | 11 | 12 |
|---|---|---|---|---|---|---|---|---|---|---|---|---|
| A | 1703 | 1766 | 1343 | 1800 | 1156 | 1653 | 1788 | 1877 | 1408 | 1665 | 1797 | 1359 |
| B | 1868 | 1747 | 1763 | 1707 | 1380 | 1756 | 1799 | 1927 | 1910 | 2466 | 1899 | 1859 |
| C | 1752 | 1651 | 1681 | 1725 | 1482 | 1692 | 1678 | 1848 | 1735 | 1789 | 2104 | 1255 |
| D | X | X | X | X | X | X | X | X | X | X | X | X |
| E | X | X | X | X | X | X | X | X | X | X | X | X |
| F | 1511 | 1537 | 1786 | 1498 | 1553 | X | X | X | X | X | X | X |
| G | 1518 | 1602 | 1753 | 1642 | 1774 | X | X | X | X | X | X | X |
| H | 1305 | 1759 | 1653 | 1829 | 1330 | X | X | X | X | X | X | X |

Figure 12

| epi27 | epi28 | epi29 | epi30 | epi31 | epi35 | epi36 | epi37 | epi38 |
|---|---|---|---|---|---|---|---|---|
| 109.71 | 113.76 | 86.51 | 115.95 | 74.47 | 106.48 | 115.18 | 120.91 | 90.70 |
| 120.33 | 112.54 | 113.57 | 109.96 | 88.90 | 113.12 | 115.89 | 124.14 | 123.04 |
| 112.86 | 106.36 | 108.29 | 111.12 | 95.47 | 109.00 | 108.10 | 119.05 | 111.77 |
| 114.30 | 110.89 | 102.79 | 112.35 | 86.28 | 109.53 | 113.06 | 121.37 | 108.50 |

| epi39 | epi40 | epi41 | epi60 | epi61 | echium* | vehicle | untreated |
|---|---|---|---|---|---|---|---|
| 107.26 | 115.76 | 87.55 | 97.34 | 99.01 | 115.05 | 96.50 | 100.04 |
| 158.86 | 122.33 | 119.76 | 97.79 | 103.20 | 112.93 | 105.78 | 114.28 |
| 115.25 | 135.54 | 80.85 | 84.07 | 113.31 | 106.58 | 117.82 | 85.68 |
| 127.12 | 124.54 | 96.05 | 93.06 | 105.18 | 111.49 | 106.70 | 100.00 |

|   | 1 | 2 | 3 | 4 | 5 | 6 | 7 | 8 | 9 | 10 | 11 | 12 |
|---|---|---|---|---|---|---|---|---|---|---|---|---|
| A | STD1 | STD1 | vehicle | vehicle | epi35 | epi35 | epi61 | epi61 | epi30 | epi30 | epi41 | epi41 |
| B | STD2 | STD2 | Untreated1 | Untreated1 | epi36 | epi36 | epi63 | epi63 | epi31 | epi31 | epi60 | epi60 |
| C | STD3 | STD3 | Untreated2 | Untreated2 | epi37 | epi37 | vehicle | vehicle | epi35 | epi35 | epi61 | epi61 |
| D | STD4 | STD4 | epi27 | epi27 | epi38 | epi38 | Untreated1 | Untreated1 | epi36 | epi36 | X | X |
| E | STD5 | STD5 | epi28 | epi28 | epi39 | epi39 | Untreated2 | Untreated2 | epi37 | epi37 | X | X |
| F | STD6 | STD6 | epi29 | epi29 | epi40 | epi40 | epi27 | epi27 | epi38 | epi38 | X | X |
| G | STD7 | STD7 | epi30 | epi30 | epi41 | epi41 | epi28 | epi28 | epi39 | epi39 | X | X |
| H | epi63 | epi63 | epi31 | epi31 | epi60 | epi60 | epi29 | epi29 | epi40 | epi40 | X | X |

|   | 1 | 2 | 3 | 4 | 5 | 6 | 7 | 8 | 9 | 10 | 11 | 12 |
|---|---|---|---|---|---|---|---|---|---|---|---|---|
| A | 363 | 354 | 1713 | 1730 | 1209 | 1777 | 1682 | 1213.00 | 1837.00 | 1750.00 | 1772.00 | 1826.00 |
| B | 608 | 566 | 1762 | 2012 | 1666 | 1894 | 1932 | 1917.00 | 2042.00 | 1882.00 | 1826.00 | 1784.00 |
| C | 954 | 954 | 2084 | 2065 | 1669 | 1856 | 2058 | 1962.00 | 1934.00 | 1854.00 | 1861.00 | 1850.00 |
| D | 1498 | 1524 | 1514 | 1630 | 1686 | 1133 | 2104 | 2333.00 | 1873.00 | 2106.00 | 143.00 | 269.00 |
| E | 1689 | 1687 | 1941 | 1970 | 1911 | 2171 | 2262 | 2095.00 | 1918.00 | 2099.00 | 160.00 | 548.00 |
| F | 2067 | 2084 | 1453 | 1428 | 1692 | 2346 | 2121 | 1951.00 | 2033.00 | 2112.00 | 140.00 | 168.00 |
| G | 2237 | 2100 | 1728 | 1966 | 1688 | 1960 | 2103 | 1840.00 | 2263.00 | 2112.00 | 262.00 | 232.00 |
| H | 1572 | 1293 | 1378 | 1984 | 1018 | 1084 | 2032 | 1758.00 | 1908.00 | 1930.00 | 167.00 | 167.00 |

|   | µg/ml |
|---|---|
| STD1 | 8.555 |
| STD2 | 4.278 |
| STD3 | 2.139 |
| STD4 | 1.069 |
| STD5 | 0.535 |
| STD6 | 0.267 |
| STD7 | 0.134 |

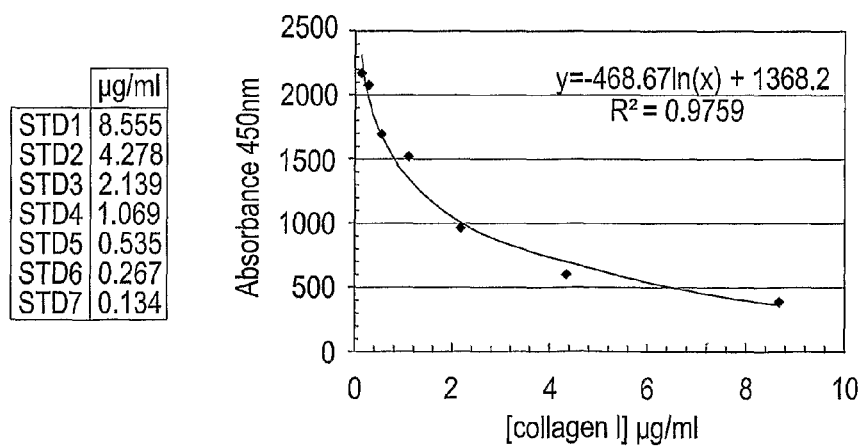

| Pepsin digests of culture media samples | | | | |
|---|---|---|---|---|
| Test oil | sample 1 | sample 1 | mean | % vehicle ctl |
| (Echium) | 0.70 | 1.14 | 0.92 | 99.14 |
| Vehicle | 0.94 | 0.91 | 0.93 | 100.00 |
| Untreated 1 | 0.86 | 0.56 | 0.71 | 76.62 |
| Untreated 2 | 0.49 | 0.51 | 0.50 | 53.87 |
| Epi27 | 1.33 | 1.09 | 1.21 | 130.61 |
| Epi28 | 0.63 | 0.60 | 0.62 | 66.37 |
| *Epi29* | *1.48* | *1.55* | *1.52* | *163.65* |
| Epi30 | 0.92 | 0.60 | 0.76 | 82.00 |
| Epi31 | 1.69 | 0.59 | 1.14 | 122.84 |
| *Epi35* | *2.28* | *0.84* | *1.56* | *168.10* |
| Epi36 | 1.02 | 0.69 | 0.85 | 92.05 |
| Epi37 | 1.02 | 0.73 | 0.87 | 94.31 |
| *Epi38* | *0.99* | *2.60* | *1.79* | *193.43* |
| Epi39 | 0.67 | 0.42 | 0.54 | 58.61 |
| Epi40 | 0.98 | 0.31 | 0.64 | 69.38 |
| Epi41 | 0.98 | 0.61 | 0.80 | 85.93 |
| *Epi60* | *3.18* | *2.83* | *3.01* | *324.34* |
| *Epi61* | *0.99* | *2.26* | *1.63* | *175.46* |

| Pepsin digests of culture dish surface | | | | |
|---|---|---|---|---|
| Test oil | sample 1 | sample 1 | mean | % vehicle ctl |
| (Echium) | 0.64 | 0.66 | 0.65 | 115.76 |
| Vehicle | 0.51 | 0.61 | 0.56 | 100.00 |
| Untreated 1 | 0.47 | 0.32 | 0.40 | 70.54 |
| Untreated 2 | 0.36 | 0.48 | 0.42 | 74.96 |
| Epi27 | 0.46 | 0.62 | 0.54 | 96.27 |
| Epi28 | 0.48 | 0.75 | 0.61 | 109.45 |
| *Epi29* | *0.54* | *0.87* | *0.70* | *125.43* |
| *Epi30* | *0.76* | *0.88* | *0.82* | *146.05* |
| Epi31 | 0.53 | 0.70 | 0.61 | 109.46 |
| *Epi35* | *0.64* | *0.72* | *0.68* | *121.27* |
| Epi36 | 0.71 | 0.47 | 0.59 | 105.45 |
| Epi37 | 0.66 | 0.48 | 0.57 | 101.17 |
| Epi38 | 0.54 | 0.47 | 0.50 | 89.52 |
| Epi39 | 0.36 | 0.47 | 0.41 | 73.65 |
| *Epi40* | *0.67* | *0.64* | *0.66* | *116.90* |
| *Epi41* | *0.85* | *0.77* | *0.81* | *144.39* |
| *Epi60* | *0.77* | *0.83* | *0.80* | *142.82* |
| *Epi61* | *0.73* | *0.74* | *0.73* | *130.64* |

| Test oil name | Epistem reference | pre-dilution | tolerated volume (µl) | required final test oil dilution |
|---|---|---|---|---|
| Diluent only | n/a | 0 | 0 | 0 |
| Rosehip - refined | epi29 | 1/10 | 3 | 0.003 |
| Borage | epi35 | 1/10 | 3 | 0.003 |
| Jacaranda | epi60 | 1/100 | 3 | 0.0003 |
| Calendula | epi61 | 1/100 | 3 | 0.0003 |
| Echium oil | epi63 | 1/10 | 10 | 0.01 |
| Rosehip - refined | epi29 | 1/10 | 3 | 0.003 |
| Borage | epi35 | 1/10 | 3 | 0.003 |
| Jacaranda | epi60 | 1/100 | 3 | 0.0003 |
| Calendula | epi61 | 1/100 | 3 | 0.0003 |

| Test oil name | To make 800µl of oil mix | | | | | | | |
|---|---|---|---|---|---|---|---|---|
| | Echium oil volume(µl) | Test oil volume(µl) | Total oil volume(µl) | x2 diluent volume(µl) | x1 diluent volume(µl) | total volume(µl) | Test oil dilution | Echium oil dilution |
| Diluent only | 0 | 0 | 0 | 0 | 800 | 800 | 0 | 0.000 |
| Rosehip - refined | 80 | 26.64 | 106.64 | 106.64 | 586.72 | 800.00 | 0.0333 | 0.10 |
| Borage | 80 | 26.64 | 106.64 | 106.64 | 586.72 | 800.00 | 0.0333 | 0.10 |
| Jacaranda | 7.2 | 2.4 | 9.6 | 9.6 | 780.80 | 800.00 | 0.0030 | 0.01 |
| Calendula | 7.2 | 2.4 | 9.6 | 9.6 | 780.80 | 800.00 | 0.0030 | 0.01 |
| Echium oil | 80 | 0 | 80 | 80 | 640.00 | 800.00 | 0.0000 | 0.10 |
| Rosehip - refined | 0 | 26.64 | 26.64 | 26.64 | 746.72 | 800.00 | 0.0333 | 0.00 |
| Borage | 0 | 26.64 | 26.64 | 26.64 | 746.72 | 800.00 | 0.0333 | 0.00 |
| Jacaranda | 0 | 2.4 | 2.4 | 2.4 | 795.20 | 800.00 | 0.0030 | 0.00 |
| Calendula | 0 | 2.4 | 2.4 | 2.4 | 795.20 | 800.00 | 0.0030 | 0.00 |

| Test oil name | Within cell culture wells | | |
|---|---|---|---|
| | Final test oil dilution | Final echium oil dilution | Echium oil:Test oil ratio |
| Diluent only | 0.0000 | 0 | 0 |
| Rosehip - refined | 0.0033 | 0.010 | 3:1 |
| Borage | 0.0033 | 0.010 | 3:1 |
| Jacaranda | 0.0003 | 0.001 | 3:1 |
| Calendula | 0.0003 | 0.001 | 3:1 |
| Echium oil | 0.0000 | 0.010 | n/a |
| Rosehip - refined | 0.0033 | 0.000 | n/a |
| Borage | 0.0033 | 0.000 | n/a |
| Jacaranda | 0.0003 | 0.000 | n/a |
| Calendula | 0.0003 | 0.000 | n/a |

Figure 16

|   | Collagen standards µg/ml | | 3 | 4 | 5 | 6 | 7 | 8 | 9 | 10 | 11 | 12 |
|---|---|---|---|---|---|---|---|---|---|---|---|---|
|   | 1 | 2 | | | | | | | | | | |
| A | 10.370 | 10.370 | 29+63 | 29+63 | 63 | 63 | 61 | 61 | x | x | x | x |
| B | 5.185 | 5.185 | 29+63 | 29+63 | 63 | 63 | 61 | 61 | x | x | x | x |
| C | 2.593 | 2.593 | 35+63 | 35+63 | 29 | 29 | Vehicle | Vehicle | x | x | x | x |
| D | 1.298 | 1.298 | 35+63 | 35+63 | 29 | 29 | Vehicle | Vehicle | x | x | x | x |
| E | 0.648 | 0.648 | 60+63 | 60+63 | 35 | 35 | Untreated | Untreated | x | x | x | x |
| F | 0.324 | 0.324 | 60+63 | 60+63 | 35 | 35 | Untreated | Untreated | x | x | x | x |
| G | 0.162 | 0.162 | 61+63 | 61+63 | 60 | 60 | x | x | x | x | x | x |
| H | 0 | 0 | 61+63 | 61+63 | 60 | 60 | x | x | x | x | x | x |

|   | 1 | 2 | 3 | 4 | 5 | 6 | 7 | 8 | 9 | 10 | 11 | 12 |
|---|---|---|---|---|---|---|---|---|---|---|---|---|
| A | 323 | 327 | 813 | 777 | 1502 | 1457 | 1106 | 1175 | x | x | x | x |
| B | 658 | 606 | 834 | 925 | 1287 | 1369 | 974 | 1068 | x | x | x | x |
| C | 1043 | 924 | 740 | 768 | 1013 | 1041 | 1137 | 1111 | x | x | x | x |
| D | 1321 | 1194 | 764 | 765 | 984 | 957 | 897 | 1208 | x | x | x | x |
| E | 1501 | 1335 | 1201 | 1251 | 1004 | 1002 | 1481 | 1471 | x | x | x | x |
| F | 1522 | 1406 | 1156 | 1202 | 1054 | 1038 | 1381 | 1274 | x | x | x | x |
| G | 1649 | 1397 | 977 | 899 | 1175 | 1100 | x | x | x | x | x | x |
| H | 1615 | 1434 | 901 | 815 | 1199 | 1097 | x | x | x | x | x | x |

$y = 1524.6 e^{-0.153x}$
$R^2 = 0.9959$

| Test oil | sample 1 | Sample 2 | mean | % vehicle ctl | mean(% vehicle control) |
|---|---|---|---|---|---|
| 29+63 | 4.56 | 4.11 | 4.33 | 193.16 | 189.47 |
| 29+63 | 4.39 | 3.94 | 4.17 | 185.78 | |
| 35+63 | 5.18 | 4.72 | 4.95 | 220.73 | 216.03 |
| 35+63 | 4.97 | 4.52 | 4.74 | 211.32 | |
| 60+63 | 2.31 | 1.56 | 1.93 | 86.21 | 91.11 |
| 60+63 | 2.50 | 1.81 | 2.15 | 96.00 | |
| 61+63 | 3.42 | 2.91 | 3.16 | 141.02 | 152.35 |
| 61+63 | 3.91 | 3.44 | 3.67 | 163.67 | |
| 63 | 0.10 | 0.30 | 0.20 | 8.78 | 24.57 |
| 63 | 1.11 | 0.70 | 0.91 | 40.36 | |
| 29 | 2.67 | 2.49 | 2.58 | 115.13 | 123.37 |
| 29 | 2.86 | 3.04 | 2.95 | 131.62 | |
| 35 | 2.73 | 2.74 | 2.74 | 121.99 | 115.88 |
| 35 | 2.41 | 2.51 | 2.46 | 109.77 | |
| 60 | 1.70 | 2.13 | 1.92 | 85.49 | 84.22 |
| 60 | 1.57 | 2.15 | 1.86 | 82.94 | |
| 61 | 2.10 | 1.70 | 1.90 | 84.70 | 101.59 |
| 61 | 2.93 | 2.39 | 2.66 | 118.49 | |
| Veh | 1.92 | 2.07 | 1.99 | 88.83 | 100.00 |
| Veh | 3.47 | 1.52 | 2.49 | 111.17 | |
| Untreated | 0.28 | 0.23 | 0.26 | 11.42 | 25.99 |
| Untreated | 0.65 | 1.17 | 0.91 | 40.57 | |

Figure 21

| | Collagen standards mg/ml | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | 10.370 | 10.370 | 29+63 | 29+63 | 63 | 63 | 61 | 61 | X | X | X | X |
| B | 5.185 | 5.185 | 29+63 | 29+63 | 63 | 63 | 61 | 61 | X | X | X | X |
| C | 2.593 | 2.593 | 35+63 | 35+63 | 29 | 29 | Vehicle | Vehicle | X | X | X | X |
| D | 1.296 | 1.296 | 35+63 | 35+63 | 29 | 29 | Vehicle | Vehicle | X | X | X | X |
| E | 0.648 | 0.648 | 60+63 | 60+63 | 35 | 35 | Untreated | Untreated | X | X | X | X |
| F | 0.324 | 0.324 | 60+63 | 60+63 | 35 | 35 | Untreated | Untreated | X | X | X | X |
| G | 0.162 | 0.162 | 61+63 | 61+63 | 60 | 60 | X | X | X | X | X | X |
| H | 0 | 0 | 61+63 | 61+63 | 60 | 60 | X | X | X | X | X | X |

| | 1 | 2 | 3 | 4 | 5 | 6 | 7 | 8 | 9 | 10 | 11 | 12 |
|---|---|---|---|---|---|---|---|---|---|---|---|---|
| A | 393 | 354 | 1713 | 1730 | 1209 | 1777 | 1682 | 1213 | X | X | X | X |
| B | 608 | 586 | 1762 | 2012 | 1565 | 1894 | 1932 | 1917 | X | X | X | X |
| C | 954 | 954 | 2084 | 2095 | 1569 | 1858 | 2058 | 1962 | X | X | X | X |
| D | 1458 | 1523 | 1514 | 1630 | 1589 | 1133 | 2104 | 2333 | X | X | X | X |
| E | 1689 | 1587 | 1941 | 1970 | 1911 | 2171 | 2282 | 2095 | X | X | X | X |
| F | 2067 | 2084 | 1453 | 1428 | 1552 | 2346 | 2121 | 1951 | X | X | X | X |
| G | 2237 | 2100 | 1728 | 1956 | 1588 | 1950 | X | X | X | X | X | X |
| H | 1572 | 1293 | 1378 | 1984 | 1018 | 1084 | X | X | X | X | X | X |

Figure 22

| Test oil | sample 1 | sample 2 | mean | % vehicle ctl | mean (% vehicle control) |
|---|---|---|---|---|---|
| 29+63 | 0.64 | 0.62 | 0.63 | 195.67 | 172.52 |
| 29+63 | 0.58 | 0.37 | 0.48 | 149.36 | |
| 35+63 | 0.33 | 0.34 | 0.33 | 104.41 | 180.53 |
| 35+63 | 0.91 | 0.74 | 0.82 | 256.64 | |
| 60+63 | 0.42 | 0.40 | 0.41 | 129.08 | 225.86 |
| 60+63 | 1.01 | 1.06 | 1.03 | 322.66 | |
| 61+63 | 0.62 | 0.41 | 0.51 | 160.02 | 200.80 |
| 61+63 | 1.15 | 0.39 | 0.77 | 241.58 | |
| 63 | 1.56 | 0.57 | 1.06 | 332.14 | 256.04 |
| 63 | 0.69 | 0.46 | 0.58 | 179.95 | |
| 29 | 0.69 | 0.49 | 0.59 | 184.41 | 283.69 |
| 29 | 0.67 | 1.78 | 1.23 | 382.98 | |
| 35 | 0.45 | 0.28 | 0.36 | 113.79 | 124.54 |
| 35 | 0.66 | 0.21 | 0.43 | 135.30 | |
| 60 | 0.66 | 0.41 | 0.54 | 167.83 | 407.04 |
| 60 | 2.19 | 1.95 | 2.07 | 646.25 | |
| 61 | 0.67 | 1.55 | 1.11 | 346.73 | 241.54 |
| 61 | 0.43 | 0.44 | 0.44 | 136.35 | |
| Veh | 0.34 | 0.41 | 0.38 | 117.52 | 100.00 |
| Veh | 0.32 | 0.21 | 0.26 | 82.48 | |
| Untreated | 0.24 | 0.32 | 0.28 | 87.72 | 100.40 |
| Untreated | 0.31 | 0.42 | 0.36 | 113.08 | |

Figure 24

|   | Collagen standards µg/ml | | 3 | 4 | 5 | 6 | 7 | 8 | 9 | 10 | 11 | 12 |
|---|---|---|---|---|---|---|---|---|---|---|---|---|
|   | 1 | 2 | 3 | 4 | 5 | 6 | 7 | 8 | 9 | 10 | 11 | 12 |
| A | 10.370 | 10.370 | 29+63 | 29+63 | 63 | 63 | 61 | 61 | x | x | x | x |
| B | 5.185 | 5.185 | 29+63 | 29+63 | 63 | 63 | 61 | 61 | x | x | x | x |
| C | 2.593 | 2.593 | 35+63 | 35+63 | 29 | 29 | Vehicle | Vehicle | x | x | x | x |
| D | 1.298 | 1.298 | 35+63 | 35+63 | 29 | 29 | Vehicle | Vehicle | x | x | x | x |
| E | 0.648 | 0.648 | 60+63 | 60+63 | 35 | 35 | Untreated | Untreated | x | x | x | x |
| F | 0.324 | 0.324 | 60+63 | 60+63 | 35 | 35 | Untreated | Untreated | x | x | x | x |
| G | 0.162 | 0.162 | 61+63 | 61+63 | 60 | 60 | x | x | x | x | x | x |
| H | 0 | 0 | 61+63 | 61+63 | 60 | 60 | x | x | x | x | x | x |

|   | 1 | 2 | 3 | 4 | 5 | 6 | 7 | 8 | 9 | 10 | 11 | 12 |
|---|---|---|---|---|---|---|---|---|---|---|---|---|
| A | 180 | 174 | 556 | 583 | 625 | 638 | 640 | x | x | x | x | x |
| B | 272 | 265 | 681 | 611 | 722 | 762 | 746 | x | x | x | x | x |
| C | 505 | 509 | 842 | 776 | 954 | 827 | 728 | x | x | x | x | x |
| D | 808 | 770 | 859 | 845 | 955 | 836 | 753 | x | x | x | x | x |
| E | 1024 | 1107 | 885 | 785 | 829 | 981 | 1030 | x | x | x | x | x |
| F | 1132 | 1161 | 770 | 836 | 820 | 940 | 956 | x | x | x | x | x |
| G | 1304 | 1272 | 735 | 727 | 651 | x | x | x | x | x | x | x |
| H | 1350 | 1299 | 842 | 799 | 673 | x | x | x | x | x | x | x |

Figure 25

| Test oil | sample 1 | sample 2 | mean | % vehicle ctl | mean (% vehicle control) |
|---|---|---|---|---|---|
| 29+63 | 2.10 | 2.11 | 2.11 | 186.22 | 169.18 |
| 29+63 | 1.60 | 1.84 | 1.72 | 152.10 | |
| 35+63 | 0.95 | 1.15 | 1.05 | 92.82 | 87.26 |
| 35+63 | 0.91 | 0.94 | 0.92 | 81.71 | |
| 60+63 | 0.84 | 1.12 | 0.98 | 86.65 | 90.54 |
| 60+63 | 1.17 | 0.97 | 1.07 | 94.43 | |
| 61+63 | 1.29 | 1.32 | 1.31 | 115.58 | 102.57 |
| 61+63 | 0.95 | 1.08 | 1.01 | 89.58 | |
| 63 | 1.77 | 1.71 | 1.74 | 153.71 | 142.42 |
| 63 | 1.34 | 1.62 | 1.48 | 131.12 | |
| 29 | 0.67 | 0.92 | 0.80 | 70.47 | 72.78 |
| 29 | 0.67 | 1.03 | 0.85 | 75.09 | |
| 35 | 0.99 | 1.05 | 1.02 | 90.23 | 94.08 |
| 35 | 1.01 | 1.20 | 1.11 | 97.94 | |
| 60 | 1.51 | 2.04 | 1.78 | 157.03 | 159.38 |
| 60 | 1.54 | 2.11 | 1.83 | 161.73 | |
| 61 | 1.76 | 1.70 | 1.73 | 152.61 | 130.41 |
| 61 | 1.20 | 1.25 | 1.22 | 108.21 | |
| Veh | 0.99 | 1.34 | 1.16 | 102.99 | 100.00 |
| Veh | 0.97 | 1.23 | 1.10 | 97.01 | |
| Untreated | 0.64 | 0.55 | 0.60 | 52.74 | 56.97 |
| Untreated | 0.72 | 0.67 | 0.69 | 61.20 | |

Figure 27

| | Collagen standards | µg/ml | 3 | 4 | 5 | 6 | 7 | 8 | 9 | 10 | 11 | 12 |
|---|---|---|---|---|---|---|---|---|---|---|---|---|
| | 1 | 2 | | | | | | | | | | |
| A | 10.370 | 10.370 | 29+63 | 29+63 | 63 | 63 | 61 | 61 | X | X | X | X |
| B | 5.185 | 5.185 | 29+63 | 29+63 | 63 | 63 | 61 | 61 | X | X | X | X |
| C | 2.593 | 2.593 | 35+63 | 35+63 | 29 | 29 | Vehicle | Vehicle | X | X | X | X |
| D | 1.296 | 1.296 | 35+63 | 35+63 | 29 | 29 | Vehicle | Vehicle | X | X | X | X |
| E | 0.648 | 0.648 | 60+63 | 60+63 | 35 | 35 | Untreated | Untreated | X | X | X | X |
| F | 0.324 | 0.324 | 60+63 | 60+63 | 35 | 35 | Untreated | Untreated | X | X | X | X |
| G | 0.162 | 0.162 | 61+63 | 61+63 | 60 | 60 | X | X | X | X | X | X |
| H | Kit control | Kit control | 61+63 | 61+63 | 60 | 60 | X | X | X | X | X | X |

| | 1 | 2 | 3 | 4 | 5 | 6 | 7 | 8 | 9 | 10 | 11 | 12 |
|---|---|---|---|---|---|---|---|---|---|---|---|---|
| A | 180 | 174 | 901 | 865 | 1194 | 1078 | 1104 | 1075 | X | X | X | X |
| B | 272 | 265 | 1126 | 948 | 959 | 940 | 1216 | 1244 | X | X | X | X |
| C | 505 | 509 | 724 | 697 | 1005 | 1165 | 1520 | 1606 | X | X | X | X |
| D | 808 | 770 | 1169 | 1131 | 1002 | 1103 | 1414 | 1440 | X | X | X | X |
| E | 1024 | 1107 | 1174 | 1229 | 1116 | 1150 | 1445 | 1509 | X | X | X | X |
| F | 1132 | 1161 | 1158 | 1039 | 1008 | 1028 | 1439 | 1374 | X | X | X | X |
| G | 1304 | 1272 | 1045 | 999 | 1070 | 1240 | X | X | X | X | X | X |
| H | 1350 | 1299 | 1185 | 1102 | 893 | 1004 | X | X | X | X | X | X |

Figure 28

| Test oil | sample 1 | sample 2 | mean | % vehicle ctl | mean (% vehicle control) |
|---|---|---|---|---|---|
| 29+63 | 0.80 | 0.89 | 0.85 | 565.78 | 470.53 |
| 29+63 | 0.42 | 0.70 | 0.56 | 375.28 | |
| 35+63 | 1.33 | 1.44 | 1.39 | 927.06 | 595.15 |
| 35+63 | 0.37 | 0.42 | 0.39 | 263.25 | |
| 60+63 | 0.37 | 0.31 | 0.34 | 227.49 | 282.57 |
| 60+63 | 0.47 | 0.54 | 0.51 | 337.65 | |
| 61+63 | 0.53 | 0.61 | 0.57 | 380.18 | 324.94 |
| 61+63 | 0.36 | 0.45 | 0.40 | 269.70 | |
| 63 | 0.35 | 0.48 | 0.41 | 277.41 | 369.07 |
| 63 | 0.66 | 0.72 | 0.69 | 460.73 | |
| 29 | 0.60 | 0.38 | 0.49 | 325.05 | 338.15 |
| 29 | 0.60 | 0.45 | 0.53 | 351.25 | |
| 35 | 0.43 | 0.38 | 0.41 | 272.60 | 328.24 |
| 35 | 0.59 | 0.56 | 0.57 | 383.89 | |
| 60 | 0.49 | 0.30 | 0.40 | 266.85 | 370.55 |
| 60 | 0.82 | 0.60 | 0.71 | 474.25 | |
| 61 | 0.45 | 0.49 | 0.47 | 312.90 | 261.03 |
| 61 | 0.33 | 0.30 | 0.31 | 209.17 | |
| Veh | 0.14 | 0.11 | 0.12 | 81.09 | 100.00 |
| Veh | 0.18 | 0.17 | 0.18 | 118.91 | |
| Untreated | 0.17 | 0.14 | 0.15 | 103.24 | 114.90 |
| Untreated | 0.17 | 0.21 | 0.19 | 126.57 | |

Figure 30

COMPOSITION FOR ACCELERATED PRODUCTION OF COLLAGEN

This application is a national phase of International Application No. PCT/GB2009/001891 filed 31 Jul. 2009 and published in the English language.

FIELD OF INVENTION

This disclosure relates generally to a topical skin care composition, and more specifically to a topical skin care composition formulated to provide accelerated production of collagen.

BACKGROUND ART

Collagen is one of the long, fibrous structural proteins whose functions are quite different from those of globular proteins such as enzymes. Collagen is the main protein of connective tissue in animals and the most abundant protein in mammals, making up about 40% of the total. It is tough and inextensible, with great tensile strength, and is the main component of cartilage, ligaments and tendons, and the main protein component of bone and teeth. Along with soft keratin, it is responsible for skin strength and elasticity, and its degradation leads to wrinkles that accompany aging. Collagen strengthens blood vessels and plays a role in tissue development. Collagen is present in the cornea and lens of the eye in crystalline form. It is also used in cosmetic surgery and burn surgery.

Collagen occurs in many places throughout the body, and in many different forms, each form being known as a type. There are at least 12 different types of collagen, with Type I collagen being the most abundant. The basic triple-helix structure of Type I collagen is the prototype for most of the other collagen types.

The other types of collagen differ from Type I collagen in the length of their triple helix and the presence or absence of globular domains at their amino or carboxyl terminal ends. Type I collagen may be found in skin, tendons, and bone, and Types I-III are recognized as playing a vital role in skin development and formation.

There is a need for skin care compositions and compositions for in-vitro administration which enhance production of collagen.

DISCLOSURE OF THE INVENTION

The present invention in a first embodiment provides a composition for topical application to the skin of animal especially a mammal, comprising stearidonic acid in combination with one or more plant lipids. The preferred source of stearidonic acid is a plant oil extract from one or more species from the *Echium* genus. The preferred species is *Echium plantagineum* L.: Purple Viper's-bugloss, Patterson's Curse.

The present invention a further embodiment provides a composition for topical application to the skin of animal especially a mammal, comprising stearidonic acid in combination with one or more CODTA's. The preferred source of stearidonic acid is a plant oil extract from one or more species from the *Echium* genus. The preferred species is *Echium plantagineum* L.: Purple Viper's-bugloss, Patterson's Curse.

Preferably the plant lipids are those, which contain a class of fatty acids known as octadecatrienoic acids (CODTA's). Preferred CODTA's are Calendic acid, Catalpic acid, α-Eleostearic acid, Jacaric acid, and Punicic acid.

Preferred sources of the CODTA's are *Calendula officinalis, Catalpa ovata, Aleurites fordii, Jacandra mimosifolia* and *Punica granatum*.

The one or more species from the *Echium* genus are selected from any combination of one or more of the following:

*Echium acanthocarpum* Svent.
*Echium aculeatum* Poir.
*Echium albicans* Lag. & Rodr.
*Echium angustifolium* Lam.
*Echium arenarium* Guss.
*Echium asperrimum* Lam.
*Echium auberianum* Webb et Berth.
*Echium bethencourtii* Santos
*Echium boissieri* Steudel
*Echium bonnetii* Coincy
*Echium brevirame* Sprague et Hutch.
*Echium callithyrsum* Webb ex Bolle
*Echium candicans* L. fil.: Pride of Madeira
*Echium creticum* L.
*Echium decaisnei* Webb
*Echium flavum* Desf.
*Echium gaditanum* Boiss.
*Echium gentianoides*
*Echium giganteum* L. fil.
*Echium handiense* Svent.
*Echium humile* Desf.
*Echium italicum* L.: Pale Viper's-bugloss
*Echium lancerottense* Lems et Holz.
*Echium leucophaeum* Webb ex Sprague et Hutch.
*Echium lusitanicum* L.
*Echium marianum* Boiss.
*Echium nervosum* Dryand. in W. T. Aiton
*Echium parviflorum* Moench: Small-flowered Viper's-bugloss
*Echium pavonianum* Boiss.
*Echium pininana* Webb et Berth.: Giant Viper's-bugloss
*Echium plantagineum* L.: Purple Viper's-bugloss, Patterson's Curse
*Echium pustulatum* Sibth. & Sm.
*Echium rosulatum* Lange: Lax Viper's-bugloss
*Echium russicum* J.F.Gmel.
*Echium sabulicola* Pomel
*Echium salmanticum* Lag.
*Echium simplex* DC.
*Echium strictum* L.f.
*Echium sventenii* Bramw.
*Echium tuberculatum* Hoffmanns. & Link
*Echium virescens* DC.: Tower of Jewels
*Echium vulgare* L: Viper's Bugloss
*Echium webbii* Coincy
*Echium wildpretii* Pears. ex Hook. fil.

In a further embodiment in accordance with the present invention there is provided a method of treating skin, comprising topically applying a composition comprising stearidonic acid in combination with one or more plant lipids to the skin.

In a further embodiment in accordance with the present invention there is provided a method of treating skin, comprising topically applying a composition comprising stearidonic acid in combination with one or more CODTA's to the skin.

In a further embodiment in accordance with the present invention there is provided the use of stearidonic acid in combination with one or more plant lipids, to accelerate collagen production in skin.

In a further embodiment in accordance with the present invention there is provided the use of stearidonic acid in combination with one or more CODTA's, to accelerate collagen production in skin.

In a further embodiment in accordance with the present invention there is provided the use of stearidonic acid or a physiologically acceptable derivatives thereof in combination with one or more plant lipids, or a physiologically acceptable derivative thereof for the manufacture of a medicament to accelerate collagen production in skin.

In a further embodiment in accordance with the present invention there is provided the use of stearidonic acid or a physiologically acceptable derivatives thereof in combination with one or more CODTA's, or a physiologically acceptable derivative thereof for the manufacture of a medicament to accelerate collagen production in skin.

A pharmaceutical composition for treating skin conditions including aged skin, comprising stearidonic acid or a physiologically acceptable derivatives thereof in combination with one or more plant lipids, or a physiologically acceptable derivative thereof, and a physiologically acceptable carrier.

A pharmaceutical composition for treating skin conditions including aged skin, comprising stearidonic acid or a physiologically acceptable derivatives thereof in combination with one or more CODTA's, or a physiologically acceptable derivative thereof, and a physiologically acceptable carrier.

In a preferred embodiment the *echium* oil is extracted from plant seed using a supercritical carbon dioxide extraction process.

DESCRIPTION OF THE DRAWINGS

FIG. 2: Cell viability in human dermal fibroblast cultures treated with test oils (first screen). Test oils were pre-diluted, 1/10, in 2 mM BSA/1.8% DMSO. Results shown are means of triplicate wells, and are expressed as a percentage of untreated control viability. The five bars for each treatment represent the five different volumes of each oil tested; from left to right they are 10 (no shading), 8, 6, 3 and 1 µl (most shaded). Cell culture medium volume in each well was 100 µl.

FIG. 4: Selected test oil dilutions and formulations of test oil mixes. *Echium* oil/test oil mixes were formulated to be added at a final volume of 10 µl in 100 µl of cell culture medium.

FIG. 6: Test plate layouts and absorbance readings for WST-1 cell viability assay for *echium* oil (Epi63) dilutions. Figures represent absorbance at 450 nm minus absorbance at 620 nm. The following wells on plate 2 gave unexpectedly low readings: A6, C2, E2, E3, F2, F3, F4—these were in samples diluted in 2 mM BSA and were not considered to be worth repeating, as results from samples diluted in 2 mM BSA/1.8% DMSO—the preferred diluent—showed good consistency.

FIG. 7: Cell viability expressed as a percentage of untreated control cell viability for cell culture wells treated with *echium* oil (Epi63) dilutions. Viable cell number is directly related to the corrected absorbance readings ($A_{450nm}-A_{620nm}$). The mean absorbance reading for untreated control culture wells was 1429.57.

FIG. 8: Plate layouts and absorbance readings from the first cytotoxicity screen of test oils.

FIG. 9: Cell viability expressed as a percentage of untreated control cell viability for cell culture wells treated with test oils dilutions—screen I. Viable cell number is directly related to the corrected absorbance readings ($A_{450nm}-A_{620nm}$). The mean absorbance reading for untreated control culture wells was 1764.17. All oils were diluted 1/10 in 2 mM BSA/1.8% DMSO.

FIG. 10: Plate layouts and absorbance readings from the second cytotoxicity screen of test oils. Two well G1 and H1 (10 µl) on plate 1 gave very low absorbance readings indicative of no WST-1 reagent being added to these wells.

FIG. 11: Cell viability expressed as a percentage of untreated control cell viability for cell culture wells treated with test oils dilutions—screen II. Viable cell number is directly related to the corrected absorbance readings ($A_{450nm}-A_{620nm}$). The mean absorbance reading for untreated control culture wells was 1235.8. All oils were diluted in 2 mM BSA/1.8% DMSO.

FIG. 12: Plate layouts and absorbance readings from the cytotoxicity screen of *echium* oil/test oil mixes. *Echium* oil/test oil mixes were formulated as detailed in Table 3.1; 10 µl of each oil mix were added to each well (100 µl cell culture medium volume). *Echium* labelled wells were treated with *echium* oil alone.

FIG. 13: Cell viability expressed as a percentage of untreated control cell viability for cell culture wells treated with *echium* oil/test oils mixes. Viable cell number is directly related to the corrected absorbance readings ($A_{450nm}-A_{620nm}$). The mean absorbance reading for untreated control culture wells was 1552.33. All oils were diluted in 2 mM BSA/1.8% DMSO.

FIG. 14: Plate layouts and absorbance readings for ELISA determination of collagen I. Collagen 1 levels were determined in pepsin digests of cell culture medium samples (coded in yellow) and pepsin digests of the tissue culture surface (coded in green), prepared in accordance with the ELISA kit manufacturer's recommendations (Cosmo Bio Co Ltd.). Collagen I standard concentrations are also given and a plot of the Collagen I standard curve is shown. Each sample comes from a separate cell culture well.

FIG. 15: Collagen I concentrations in assay samples. Collagen I concentration are expressed in µg/ml, and were determined using the formula calculated from the standard curve of the ELISA assay. Oil mixes highlighted in pale blue indicate samples which demonstrated >10% increase in collagen concentration relative to levels observed in cultures treated with diluent alone (vehicle=2 mM BSA/1.8% DMSO), for a given set of samples (medium or culture surface). Figures in bold are for oil mixes that increased levels of collagen I in both culture media and adhered to the cell culture surface.

FIG. 16: Formulation of test oils. Rosehip (refined), borage, *jacaranda* and *calendula* oil were formulated with and without *echium* (base) oil, in accordance with data obtained from the earlier study; 200 μl of each test oil mix was added to 2 ml culture medium. The diluent employed was 2 mM BSA/1.8% DMSO—maximum DMSO achieved in culture wells was 0.18%.

FIG. 21: Donor 1—collagen I values determined from standard curve for media samples.

FIG. 22: Donor 1—plate layout and raw absorbance data for plate (adhered collagen) samples. Samples with the same label in adjacent columns are replicate samples from the same culture well. Samples, with same label in the same column are from different culture wells. Absorbance was determined at 450 nm.

FIG. 24: Donor 1—collagen I values determined from standard curve for plate (adhered collagen) samples.

FIG. 25: Donor 2—plate layout and raw absorbance data for media samples. Samples with the same label in adjacent columns are replicate samples from the same culture well. Samples with same label in the same column are from different culture wells. Absorbance was determined at 450 nm.

FIG. 27: Donor 2—collagen I values determined from standard curve for media samples.

FIG. 28: Donor 2—plate layout and raw absorbance data for plate (adhered collagen) samples. Samples with the same label in adjacent columns are replicate samples from the same culture well. Samples with same label in the same column are from different culture wells. Absorbance was determined at 450 nm.

FIG. 30: Donor 2—collagen I values determined from standard curve for plate (adhered collagen) samples.

DETAILED DESCRIPTION OF THE INVENTION

Figure 1:
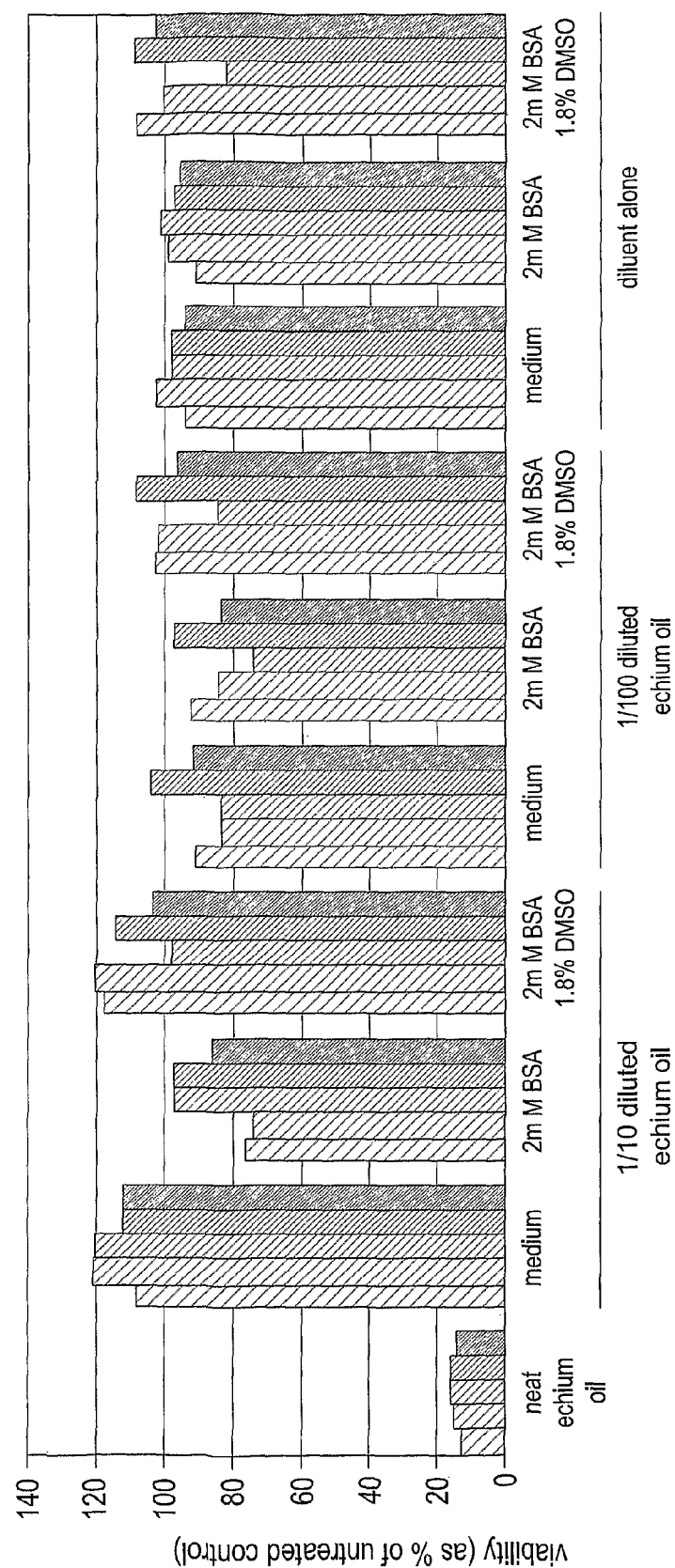
FIG. 1: Cell viability in human dermal fibroblast cultures treated with *echium* oil formulated in three different diluents. *Echium* oil was either used neat, or diluted in cell culture medium, 2 mM BSA or 2 mM BSA/1.8% DMSO. Results shown are means of triplicate wells, and are expressed as a percentage of untreated control viability. The five bars for each treatment represent the five different volumes of each dilution tested; from left to right they are 10 (no shading), 8, 6, 3 and 1 µl (most shaded). Cell culture medium volume in each well was 100 µl.

It had previously been known that stearidonic acid, and *echium* oil as a source of stearidonic acid, can beneficially be used to improve the appearance of skin. However the biological function of the stearidonic acid or *echium* oil in promoting this activity has not been determined.

Furthermore, it is also previously known that octadecatrienoic acids (CODTAs) such as Calendic acid, Catalpic acid, α-Eleostearic acid, Jacaric acid, and Punicic acid, and plant lipids as a source of octadecatrienoic acids, can have a role in the regeneration of skin.

Against this background, the present inventors decided to study the effect of a combination of stearidonic acid with octadecatrienoic acid on collagen production in vitro.

Surprisingly, they determined that combinations stearidonic acid, including *echium* oil as a source of stearidonic acid, and octadecatrienoic acid, including different plant lipids as a source of octadecatrienoic acids, increased collagen I secretion in human dermal fibroblast cultures, by increasing both the levels of soluable collagen and adhered collagen I. This ability of these compounds to promote collagen I production had not previously been identified.

Eight test oil mixes increased the amount of measurable collagen I in pepsin digests of the cell culture surface (representing secreted collagen that had adhered to the wall and the base of the cell culture wells containing the treated fibroblasts): rosehip (refined), borage, *jacaranda*, *calendula*, pomegranate, borage (refined), and the base, *echium* oil. These data are illustrated in the accompanying figures. Four oil mixes—rosehip (refined), borage, *jacaranda* and *calendula*—can be seen to have increased soluble collagen I in the cell culture medium and adhered collagen I on the cell culture surface. Moreover, Jacaric acid (an octadecatrienoic acid) in combination with the Stearidonic acid was found to strongly induce collagen I secretion by human dermal fibroblasts. Calendic acid (also a octadecatrienoic acid) had similar potency to Jacaric acid. These surprising findings could not have been predicted, and is not obvious from, existing information regarding these materials. They also demonstrate that stearidonic acid and octadecatrienoic acid can have a synergistic effect to promote collagen production.

By promoting collagen production, it can be expected that compositions containing a combination of stearidonic acid, and *echium* oil as a source of stearidonic acid, with octadecatrienoic acid, and plant lipids as a source of octadecatrienoic acid, would have much utility as topical cosmetic formulations. Until the present invention, it had not been appreciated that a combination of stearidonic acid, and *echium* oil as a source of stearidonic acid, in combination with octadecatrienoic acid, and plant lipids as a source of octadecatrienoic acid, can act to promote collagen production in the skin, and therefore have an advantageous use as a topical formation for application to the skin.

A first aspect of the invention provides a composition for topical application to the skin of animal comprising stearidonic acid in combination with one or more octadecatrienoic acids (CODTAs).

Stearidonic acid is an ω-3 essential fatty acid, sometimes called moroctic acid. It is biosynthesized from alpha-linolenic acid by the enzyme delta-6-desaturase. Natural sources of this fatty acid are the seed oils of hemp, blackcurrant and *echium*, and the cyanobacterium spirulina. It has the chemical formula: $O_{18}H_{28}O_2$.

Stearidonic acid can be obtained in a chemically pure form from a number of different suppliers. For example, Cayman Chemical (http://www.caymanchem.com/) supplies Stearidonic Acid ethyl ester as product number 10006856.

However, preferably for the composition of the present invention stearidonic acid is present as part of an extract from a natural source, such as a plant or seed oil extract. Such plant or seed oil extracts are widely available; for example, hemp oil containing stearidonic acid can be obtained commercially from a wide variety of suppliers. Other sources of stearidonic acid include black current oil extract, which is again obtainable from a variety of different sources.

Preferably the composition of this aspect of the invention comprises a plant oil extract from a species from the *Echium* genus as the source of the stearidonic acid. A list of species of the *Echium* genus is provided able under paragraph [0010] above, from which suitable extracts can be prepared. Preferably the plant oil extract is from *Echium plantagineum* L.: Purple Viper's-bugloss, Patterson's Curse. Preferably the oil extract contains about 13% stearidonic acid.

*Echium* oil is produced from the plant seed of *Echium plantagineum*, also known as Purple Viper's Bugloss. This oil can be obtained from a wide variety of suppliers: for example, G4/SSD Ltd (Orford Hall, Binbrbok Business Park, Brookenby, Market Rasen, Lincolnshire LN8 6HF). The *echium* oil produced by G4/SSD Ltd has an excellent balance of essential fatty acids, with approximately 45% n-3, including 13% stearidonic acid (SA), 25% n-6, including 10% gamma linolenic acid (GLA), and 18% n-9 fatty acids. *Echium* oil contains two fatty acids that are not normally found in one singular natural seed oil, namely gamma linolenic acid (GLA) and stearidonic acid (SA). These two EFAs are vital as starting points in the formation of longer chain fatty acids, prostaglandins and other metabolites. Cold-pressed *echium* oil retains most of the antioxidants that are beneficial not only to help preserve the natural oil, but they are also being proved to be beneficial as active ingredients in promoting good health.

In addition to a stearidonic acid, and *echium* oil as a source of stearidonic acid, the composition of this aspect of the invention also comprises one or more octadecatrienoic acids (CODTAs).

By "octadecatrienoic acid" we include that the composition include one or more of these types of polyunsaturated fatty acid compounds Octadecatrienoic acids can be readily obtained from a variety of different chemical suppliers; for example, Sigma-Aldrich supplied a wide range of such compounds.

Preferably the composition comprises one or more plant lipids as the source of the octadecatrienoic acid. By "one of more plant lipids", we include that the composition includes lipids extracted from one or more different plant sources. For example, a composition of the invention which has plant lipid from *Borago officinalis*, in addition to the stearidonic acid, specifically *echium* oil as a source of stearidonic acid, is considered to be a composition of this aspect of the invention.

Such plant lipid can be obtained from a variety of different natural sources. The following plant lipids are examples of those that can be used in the composition of this aspect of the invention: rosehip oil (cold pressed; organic; and refined) can be obtained from Seatons (http://www.seatons-uk.co.uk/); pomegranate oil (Seatons); Tung oil (http://www.made-in-china.com/); borage oil (including refined borage oil; Seatons); Hempseed oil (Seatons); Flax oil (http://www-.bulknaturaloils.com/); wheat germ oil (Seatons); camelina oil (Seatons); *jacaranda* oil (G4/SSD Ltd, details above); *calendula* oil (Springdale).

Preferably the plant lipid is borage oil (*Borago officinalis*), wheat germ oil (*Triticum vulgare*) rosehip oil (refined; *Rosa mosqueta*), *jacaranda* oil (*Jacandra mimosifolia*), and/or *calendula* oil (*Calendula officinalis*).

Preferably the octadecatrienoic acid is Calendic acid, Catalpic acid, α-Eleostearic acid, Jacaric acid and/or Punicic acid.

A particularly preferred embodiment of the invention is wherein the composition comprises plant oil extract from *Echium plantagineum* L.: Purple Viper's-bugloss, Patterson's Curse, and the plant lipid is borage oil (*Borago officinalis*). A further particularly preferred embodiment of the invention is wherein the composition comprises plant oil extract from *Echium plantagineum* L.: Purple Viper's-bugloss, Patterson's Curse, and the plant lipid is wheat germ oil (*Triticum vulgare*).

The composition of this aspect of the invention can have range of ratios of stearidonic acid/octadecatrienoic acid (CODTAs): for example, from 10:1 to 1:10. However, preferably the ratio is about 1:1; 2:1; 3:1; 4:1 or 5:1. Most preferably the ratio is about 3:1.

Also, as appropriate according to the embodiment of the composition of this aspect of the invention can have range of ratios of plant oil extract to plant lipid ratio: for example, from 10:1 to 1:10. However, preferably the ratio is about 1:1; 2:1; 3:1; 4:1 or 5:1 plant oil extract to plant lipid ratio. Most preferably the ratio is about 3:1.

As can be appreciated by the skilled person, the composition of this aspect of the invention can also have a range of different quantities of the stearidonic acid, and *echium* oil as a source of stearidonic acid, and octadecatrienoic acid, and plant lipids as a source of octadecatrienoic acid, depending on the potency of the active ingredients in increasing the production of collagen; the amount of composition to be applied; and the frequency of the application of the topical composition to the skin.

By way of guidance, the examples section set out below provides information on the ratios and amounts of the *echium* oil extract and plant lipids that can act promote collagen production. The examples also provide guidance for a series of assays to determine the effect of the composition on collagen production. For example, where the composition of the invention comprises *echium* oil and borage oil, it is shown in the examples that 10% *echium* oil and 3.33% borage oil in the final composition can act to promote collagen production. For refined rosehip oil, again a 10% *echium* oil and 3.33% borage oil mixture can be used. For *jacaranda* and *calendula*, 1% *echium* oil and 0.3% plant lipid can be used.

Supercritical carbon dioxide is now well established as a solvent for use in extraction. This is for a number of reasons. It can generally penetrate a solid sample faster than liquid solvents because of it's high diffusion rates, and can rapidly transport dissolved solutes from the sample matrix because of it's low viscosity. There are also of course less solvent residues present in the products. When used to prepare plant extracts, supercritical carbon dioxide extraction processes can provide an extract having less than 0.1% contamination.

The inventors have determined that plant oils and plant lipids extracted from source materials using supercritical carbon dioxide extraction processes retain greater ability to promote increased collagen production than oils and lipids extracted using other methods.

Hence a further preferred embodiment of this aspect of the invention is wherein the plant oil extract and plant lipid is extracted from plant seed using a supercritical carbon dioxide extraction process. Supercritical carbon dioxide extraction from natural products can be performed by a number of different companies; for example, Botanix (http://botanix.co.uk/index.html) and NATECO$_2$(http://www.nateco2.de/index.htm)

The first aspect of the invention provides a composition for topical application to the skin of animal. Preferably the animal is a human.

There are a number of ways in which the composition according to the first aspect of the invention can be formulated for topical administration to the skin of an animal.

Thus, for example, the composition may be in the form of a powder, liquid, ointment, cream, gel, hydrogel, aerosol, spray, micelle, transdermal patch, liposome or any other suitable form that allows for the composition to be topically administered. The formulation may therefore be one that can be applied by spreading or by spraying onto the skin. It will be appreciated that the vehicle of the composition of the invention should be one which is well tolerated by the subject to whom it is given. The formulation can also contain further ingredients, such as perfumes, colorants, preservatives, or further biologically active ingredients.

For application topically to the skin, the composition of the invention can be formulated as a suitable ointment containing the active ingredients suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

However it is preferred that the composition of the invention is formulated as particles in an emulsion gel. It is thought that such a formulation will beneficially allow the composition of the invention to be solubilised to facilitate effective delivery, especially to the skin. Preferred formulation technology include the 'nanoemulsions' prepared by Malvern Cosmeceutics Limited (http://www.malceutics.com/index.html).

A further aspect of the invention provides a pharmaceutical composition comprising a composition according to the first aspect of the invention and a pharmaceutically acceptable excipient. A "pharmaceutically acceptable vehicle" as referred to herein is any physiological vehicle known to those of ordinary skill in the art useful in formulating pharmaceutical compositions.

A further aspect of the invention provides a method of treating skin comprising topically applying a composition or a pharmaceutical composition according to the previous aspects of the invention to the skin.

A further aspect of the invention provides a composition or a pharmaceutical composition according to the previous aspects of the invention for increasing collagen production in skin.

A further aspect of the invention provides a composition or a pharmaceutical composition according to the previous aspects of the invention use as a medicament for increasing collagen production in skin.

A preferred embodiment of each of the above further aspects of the invention is where the composition comprises plant oil extract from *Echium plantagineum* L.: Purple Viper's-bugloss, Patterson's Curse, and the plant lipid is borage oil (*Borago officinalis*) and/or wheat germ oil (*Triticum vulgare*).

EXPERIMENTAL EXAMPLES

Example 1

An In Vitro Study to Determine the Effect of Applied Lipids on Fibroblast Collagen Synthesis Experiments were undertaken to determine the efficacy of plant-derived lipids use in combination with *echium* oil in promoting collagen I synthesis in human dermal fibroblast cultures. Human dermal fibroblast cultures derived from explant cultures of human skin, following enzymatic removal of the epidermis, provide a useful model for skin toxicity screening, determining the efficacy of UV protective agents and studying agents that may modify gene/protein expression within the dermis. This study was performed in order to determine the efficacy of a range of plant-derived oils in promoting collagen I secretion by dermal fibroblasts. Secreted collagen I was assayed in pepsin digests of the cell culture medium and pepsin digests of the cell culture surface by ELISA.

Experimental Methods: Human dermal fibroblasts (originally derived from explant cultures of normal human breast dermis) were cultured under standard conditions. A range of test oils supplied by the client were initially screened for cytotoxicity using a 96-well format, formazan-based, cell viability assay; this assay employed a single dose of test oil, with viability being measured after 48 hours. From this assay, a maximum tolerated dilution of each test oil was chosen. Subsequently, mixtures of the test oils with *echium* oil (which was chosen to be the base oil) were prepared at a ratio of one part test oil to three parts *echium* oil. These test oil/*echium* oil mixes were also screened for cytotoxicity, prior to being employed in a 6 well plate format assay. Cells were exposed to the oil mixes for a period of three days. Cell culture media, cells and the culture plates were all harvested and stored at −80° C., prior to analysis. A commercial ELISA kit was employed in order to determine the concentration of collagen I in the culture medium and the amount of secreted collagen that had adhered to the cell culture well.

Detailed Methods:

Culture of Human Dermal Fibroblasts

Human dermal fibroblasts were maintained in DMEM, with 10% FCS, L-glutamine (2 mM), penicillin (100 IU/ml) and streptomycin (100 µg/ml), at 37° C., in 95% air/5% CO$_2$ atmosphere, with 95% relative humidity. For use in cytotoxicity and collagen I assays, cells were harvested by trypsin/EDTA treatment.

Test Agents

The test agents were supplied in liquid form, at room temperature, by the client. The test agents are listed in Table 1 below together with their reference code.

TABLE 1

| Test agent | Code |
| --- | --- |
| Echium oil | Epi63 |
| Rosehip oil - cold pressed | Epi27 |
| Rosehip oil - organic | Epi28 |
| Rosehip oil - refined | Epi29 |
| Pomegranate | Epi30 |
| Tung | Epi31 |
| Borage | Epi35 |

TABLE 1-continued

| Test agent | Code |
| --- | --- |
| Hemp | Epi36 |
| Flax | Epi37 |
| Wheatgerm | Epi38 |
| Carmelina | Epi39 |
| Borage - refined | Epi40 |
| Echium seed | Epi41 |
| Jacaranda | Epi60 |
| Calendula | Epi61 |

Cytotoxicity Screening of Test Agents.

Human dermal fibroblasts were plated at $2 \times 10^4$ cells per well (100 µl volume) in 96 well plates. After 48 hours, the medium was changed and wells were treated with test oils, either alone or in combination with *echium* oil. Cells were exposed to the oils for 48 hours; at the end of this period, viable cell number was determined using WST-1 Quick-cell proliferation assay (BioVision Inc.). For the WST-1 assay, the medium was refreshed in each culture well prior to the addition of 10 µl of assay reagent. Cells were incubated for 2 hours at 37° C., after which time the absorbance at 450 nm and 620 nm was determined using an Anthos H III plate reader.

Determination of Collagen I Secretion

Cells were seeded at $5 \times 10^5$ cells/well in 6 well plates. After 24 hours, the medium was changed and cells were treated with test oil mixes. Cells were exposed to test oil mixes for 72 hours, with medium and test oils being refreshed daily. At the end of the exposure period, the medium was harvested from the cell culture wells and stored at −80° C. The cells were harvested from the plate by scraping with a rubber policeman, and both the harvested cells and the culture dish were stored at −80° C., also. Collagen I secretion was determined by ELISA (Cosmo Bio Co. Ltd., Japan), using pepsin digests of both the cell culture media samples and the cell culture well surface. ELISA and pepsin digestions were carried out according to the manufacturer's instructions, with absorbance at 450 nm being determined using an Anthos H III plate reader.

Results: The base, *echium* oil was found to be well tolerated by the dermal fibroblasts at a final dilution of 1/100—a vehicle of 2 mM BSA/1.8% DMSO was chosen as a diluent. Subsequently, all test oils were assayed for cytotoxicity at an initial dilution of 1/100-1/1000. Ten of the test oils were tolerated within dilution; these were rosehip (cold pressed), rosehip (refined), pomegranate, borage, hemp, flax, wheatgerm, carmelina, borage (refined) and *echium* seed. Four oils required further dilution in the range 1/1000-10,000 in order to find a tolerated concentration; these oils were rosehip (organic), tung, *jacaranda* and *calendula*. Dilutions of *echium* oil and each test oil were then calculated to provide *echium*/test oil mixes with a 3:1 ratio, which did not exceed the tolerated concentration of either test or *echium* oil when added to the cell cultures. It was demonstrated that all the *echium*/test oil mixes had no associated cytotoxicity, and so they were all tested in the three day exposure assay to determine their effects on collagen I secretion. Four *echium*/test oil mixes increased collagen I in both the cell culture medium and the amount of collagen adhered to the cell culture plates; the test oils were rosehip (refined), borage, *jacaranda* and *calendula*). Three other test oils were associated with increases in collagen I in the culture medium (rosehip—cold pressed, tung and wheatgerm); four oils increased the amount of collagen adhered to the cell culture well (pomegranate, *echium*, borage—refined and *echium* seed). Three test oils had little effect on collagen I secretion (rosehip—organic, hemp and flax), and one resulted in an apparent reduction in collagen I secretion (carmelina).

Results and Discussion *Echium* oil was well tolerated by human dermal fibroblasts at dilutions up to 1/100 *Echium* oil was either added neat to cell culture wells, or formulated in one of three diluents—normal cell culture medium, 2 mM BSA and 2 mM BSA/1.8% DMSO; BSA was chosen as it can act as a carrier molecule and DMSO enhances cellular uptake. Dilutions of 1/10, 1/100 and 1/1000 were prepared in each diluent. A range of volumes of each *echium* oil dilution were tested: 10, 8, 6, 3, and 1 µl were added to triplicate wells containing 100 µl of cell culture medium.

FIG. 1 shows the relative viable cell number in fibroblast cultures treated with the different *echium* oil preparations. *Echium* dilutions of 1/10 in all diluents were well tolerated, with viabilities within the expected range. Neat *echium* oil was toxic to the fibroblasts.

From these results it was decided that the 2 mM BSA/1.8% DMSO diluent was suitable for use, in combination with the *echium* oil. This diluent was selected in preference as it had the potential to enhance uptake of the oil by the fibroblast cells, and was used as a diluent in the screening of the other, individual oils. It was also decided that 10 µl of the 1/10 dilution of the *echium* oil (equivalent to 1/100 final dilution) would be set as the maximum permitted dose of *echium* oil in the subsequent assay of test oil mixes.

Test oils demonstrated a wide range of tolerability. Dilutions of 1/10 in 2 mM BSA/1.8% DMSO were prepared for all test oils and used for an initial cytotoxicity screen, with diluted test oil volumes of 1-10 µl being added to cell culture wells containing 100 µl of medium (giving final dilution in the range of 1/100 to 1/1000). If test oils demonstrated cytotoxicity over this dilution range, the screen was repeat using test oil pre-diluted at 1/100.

Figure 3:
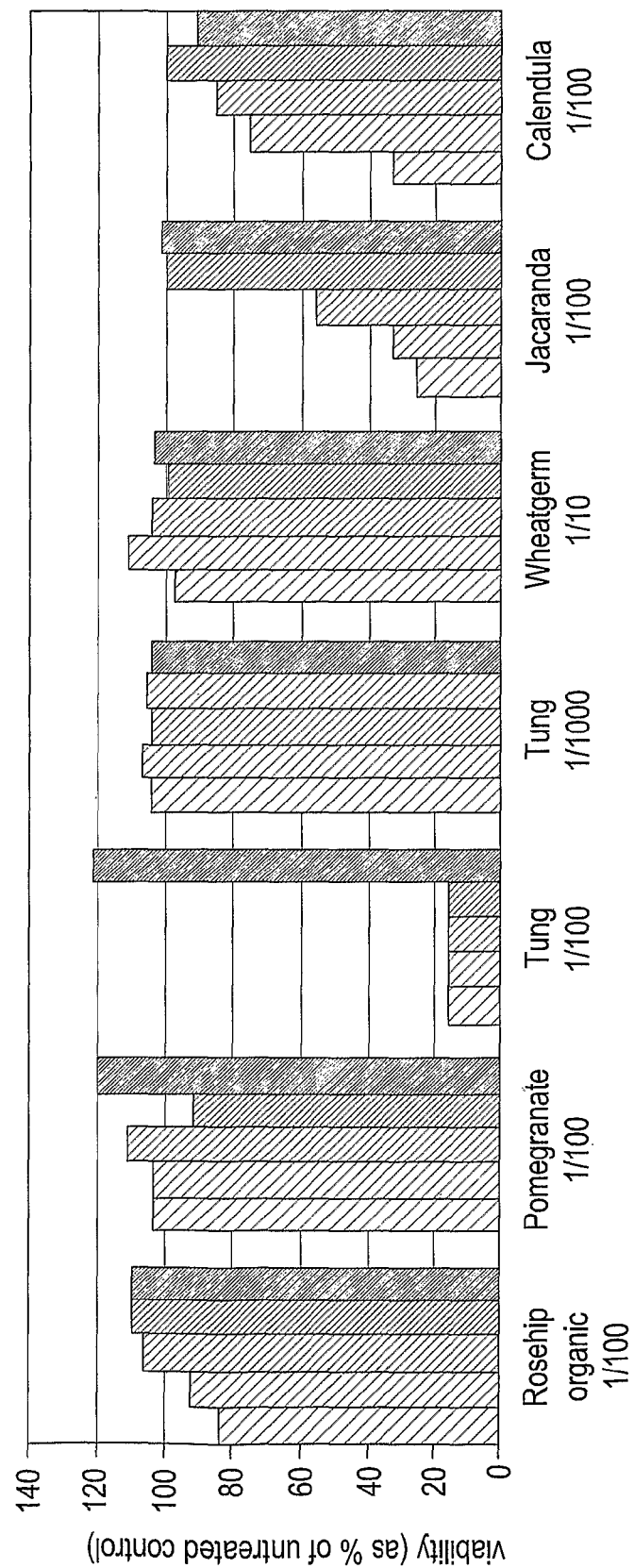
FIG. 3: Cell viability in human dermal fibroblast cultures treated with test oils (second screen). Test oils were prediluted, as indicated, in 2 mM BSA/1.8% DMSO. Results shown are means of triplicate wells, and are expressed as a percentage of untreated control viability. The five bars for each treatment represent the five different volumes of each oil tested; from left to right they are 10 (no shading), 8, 6, 3 and 1 µl (most shaded). Cell culture medium volume in each well was 100 µl

The results from the test oil screen are shown in FIG. 2. The majority of the test oils were tolerated within the initial dilution range that was tested; however six oils were re-tested in order to confirm a tolerated dilution: these oils were rosehip (organic), pomegranate, tung, wheatgerm, *jacaranda* and *calendula*. The data from this second round of screening are shown in FIG. 3. The two rounds of screening were sufficient to select a tolerated volume of each test oil. These data were then used to calculate *echium*/test. oil combination volumes that were to be assayed for their effect on collagen I secretion. Where possible, a conservative approach was used in deciding the appropriate dilution of test oil to select.

The tolerated dilution of test oils and the volumes used in making test oil mixes, using a set ratio of 3 parts *echium* oil to 1 part test oil are shown in FIG. 4. It can be seen from FIG. 4 that for some test oil mixes the final dilution of *echium* oil that could be achieved in a cell culture cell (100 µl volume) was less than 1/100 (the maximum tolerated dilution of *echium* oil), due to the limiting cytotoxicity of the test oil; these test oil mixes were with rosehip (organic), rosehip (cold-pressed), tung, *jacaranda* and *calendula*.

All test oil mixes were subject to a final round of cytotoxicity screening. All were found to be non toxic (data may be found in FIGS. 6 to 15). FIG. 3: Cell viability in human dermal fibroblast cultures treated with test oils (first screen).

Test oils were pre-diluted, 1/10, in 2 mM BSA/1.8% DMSO. Results shown are means of triplicate wells, and are expressed as a percentage of untreated control viability. The five bars for each treatment represent the five different volumes of each oil tested; from left to right they are 10 (no shading), 8, 6, 3 and 1 µl (most shaded). Cell culture medium volume in each well was 100 µl. FIG. 3: Cell viability in human dermal fibroblast cultures treated with test oils (second screen).

Test oils were pre-diluted, as indicated, in 2 mM BSA/ 1.8% DMSO. Results shown are means of triplicate wells, and are expressed as a percentage of untreated control viability. The five bars for each treatment represent the five different volumes of each oil tested; from left to right they are 10 (no shading), 8, 6, 3 and 1 µl (most shaded). Cell culture medium volume in each well was 100 µl. FIG. 4: Selected test oil dilutions and formulations of test oil mixes. *Echium* oil/test oil mixes were formulated to be added at a final volume of 10 µl in 100 µl of cell culture medium.

Rosehip (refined), borage, *jacaranda* and *calendula* test oil mixes all increased collagen I secretion by human dermal fibroblasts. ELISA analysis of pepsin digests of cell culture media samples demonstrated that 7 test oil mixes increased the amount of measurable secreted collagen I, relative to levels from cultures treated: these oils were rosehip (refined), borage, *jacaranda, calendula*, rosehip (cold-pressed), tung and wheatgerm. Eight test oil mixes increased the amount of measurable collagen I in pepsin digests of the cell culture surface (representing secreted collagen that had adhered to the wall and the base of the cell culture wells containing the treated fibroblasts): rosehip (refined), borage, *jacaranda, calendula*, pomegranate, borage (refined), *echium* seed and the base, *echium* oil.

Figure 5:
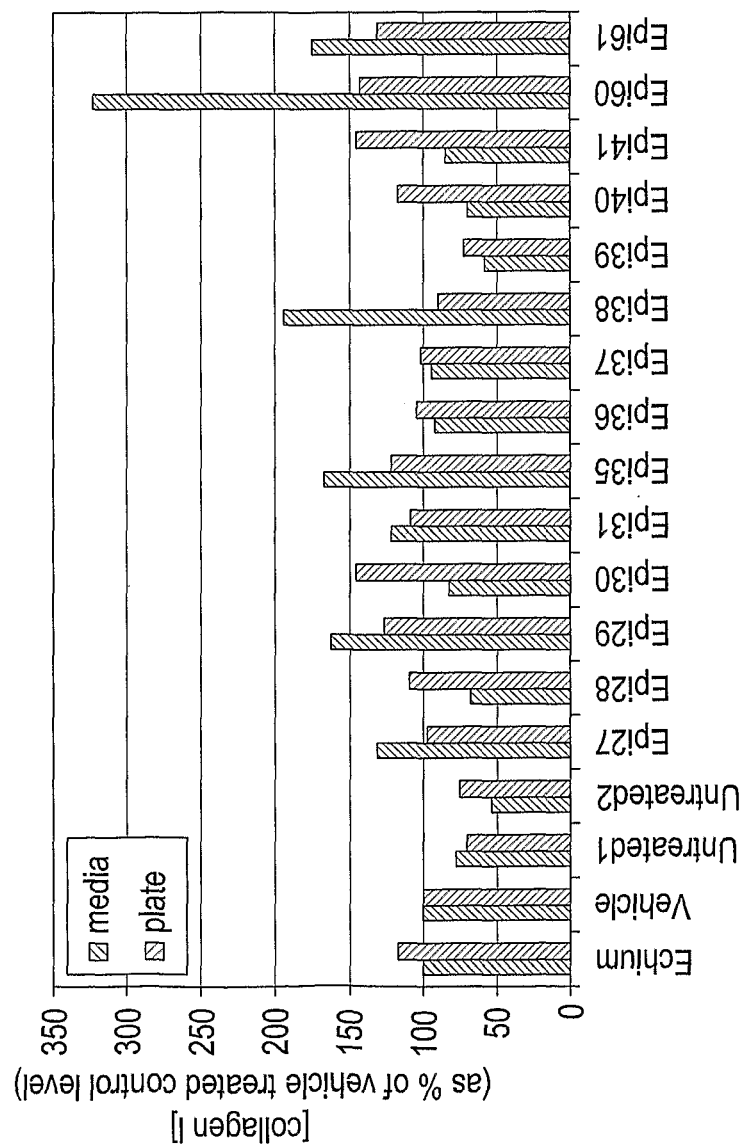
FIG. 5: Effect of test oil mixes on collagen I secretion by human dermal fibroblasts. Collagen I levels were determined by ELISA (Cosmo Bio Co Ltd.) and are expressed as a percentage of the levels observed in samples from cultures treated with diluent (vehicle) alone. Pepsin digests of both cell culture medium, and the cell culture surface (plate) from each treated culture well were analysed. Each bar represents the mean of replicate samples. The coding of each test oil is shown on the right-hand side of the graph. Test oil mixes (3:1, *echium* oil:test oil ratio) were formulated as detailed in FIG. 4.

These data are illustrated in FIG. 5. Four oil mixes— rosehip (refined), borage, *jacaranda* and *calendula*—can be seen to have increased soluble collagen I in the cell culture medium and adhered collagen I on the cell culture surface. Of these four oil mixes, *jacaranda* showed the greatest efficacy; the *jacaranda* and *calendula* mixes were also very potent, with final test oil dilutions of 3/10,000 and *echium* dilutions of 9/10,000 being achieved in the cell culture wells.

The data obtained also showed that treatment with the diluent itself (2 mM BSA/1.8% DMSO) increase collagen I secretion, relative to levels observed in untreated control cultures. This may simply reflect the diluents ability to increase the uptake of media components that positively regulate collagen I secretion.

FIG. 5: Effect of test oil mixes on collagen I secretion by human dermal fibroblasts. Collagen I levels were determined by ELISA (Cosmo Bio Co Ltd.) and are expressed as a percentage of the levels observed in samples from cultures treated with diluent (vehicle) alone. Pepsin digests of both cell culture medium, and the cell culture surface (plate) from each treated culture well were analysed. Each bar represents the mean of replicate samples. The coding of each test oil is shown on the right-hand side of the graph. Test oil mixes (3:1, *echium* oil:test oil ratio) were formulated as detailed in FIG. 4.

Conclusions *Jacaranda* oil, in combination with the base, *echium* oil, was found to strongly induce collagen I secretion by human dermal fibroblasts, under the culture conditions employed in this study. *Calendula* oil had similar potency to *jacaranda* oil, although its efficacy at increasing collagen I secretion was not so great. Rosehip (refined) and borage had similar efficacy to *calendula*, although they were tested at a ten-fold higher final concentration. Treatment with these four oils was associated with increased collagen I in both the cell culture medium, and that adhered to the cell culture well. Other oils were associated with increases in one or the other of these two parameters.

Example 2

An Investigation of the Ability of Applied Lipids to Increase Collagen Secretion by Human Fibroblasts In Vitro Summary To confirm the ability of test oil and test oil combinations to enhance levels of collagen in cultures of human dermal fibroblasts.

Previously, a range of test oils were screened for cytotoxicity and their ability to increase levels of collagen in cultures of human dermal fibroblasts. In this study the test oils that had demonstrated greatest efficacy in increasing levels of measurable collagen were re-tested, including borage, refined rosehip, *jacaranda* and *calendula* oils; these oils were tested alone and in combination with the base oil, *echium*. Both adhered collagen and collagen in the tissue culture medium were assayed. Two sets of human dermal fibroblast cultures, derived from donor skin from two separate individuals, were used in this study.

The data obtained confirmed that the test oil/*echium* oil combinations increased the amount of measurable collagen in the human fibroblast cultures. This effect was observed in samples treated with vehicle alone, but as the vehicle was also able to increase collagen levels in the culture medium this is not so surprising.

The ability of the test oils to increase the levels of extracellular collagen in human dermal fibroblast cultures in vitro was confirmed. There was some variation in the response profile of fibroblasts derived from different skin donors, but all the oils demonstrated an ability to increase the levels of adhered collagen, relative to vehicle-treated and untreated control cultures.

Introduction

Human dermal fibroblast cultures derived from explant cultures of human skin, following enzymatic removal of the epidermis, provide a useful model for skin toxicity screening, determining the efficacy of UV protective agents and studying agents that may modify gene/protein expression within the dermis. In a previous study, dermal fibroblast cultures were employed to examine the effect of test items on collagen secretion. Secreted collagen may be found in the culture media and also adheres to the culture vessel/well in which the cells are grown. A collagen I-specific ELISA can be employed to quantify collagen levels in both these compartments.

Procedures

Culture of Human Dermal Fibroblasts

Human dermal fibroblast cultures were established from breast skin samples obtained from two separate donors undergoing surgical procedures for cosmetic purposes. Dermal fibroblasts were maintained in DMEM, with 10% FCS, L-glutamine (2 mM), penicillin (100 IU/ml) and streptomycin (100 µg/ml), at 37° C., in 95% air/5% $CO_2$ atmosphere, with 95% relative humidity. For collagen I assays, cells were harvested by trypsin/EDTA treatment.

Treatment of Fibroblast Cultures with Test Items

The test items were supplied in liquid form, at room temperature, by the client. Test items were formulated according to the details in FIG. 16. Cells were seeded at $5 \times 10^5$ cells/well in 6 well plates. After 24 hours, the medium was changed and cells were treated with test oil mixes, which were added at a final volume of 200 µl in 2 ml of culture medium. All treatments were tested on fibroblast cultures derived from skin samples from two donors. Cells were exposed to test oil mixes for 72 hours, with medium and test oils being refreshed daily.

Four culture wells were treated with each test item or test item combination, or were treated with vehicle, or left untreated. At the end of the exposure period, the medium was harvested from all the cell culture wells, transferred to a sterile 7 ml tube and stored at −80° C. The cells were harvested from two culture wells for each treatment by scraping with a rubber policeman, and transferred to a sterile 1.5 ml tube. The harvested cells and the culture dish were stored at −80° C.

Determination of Secreted Collagen Levels in Fibroblast Cultures

Collagen I secretion was determined by ELISA (Cosmo Bio Co. Ltd., Japan), using pepsin digests of both the cell culture media samples and the cell culture well surface. ELISA and pepsin digestions were carried out according to the manufacturer's instructions, with absorbance at 450 nm being determined using an Anthos H III plate reader.

Results and Discussion

Figure 17:
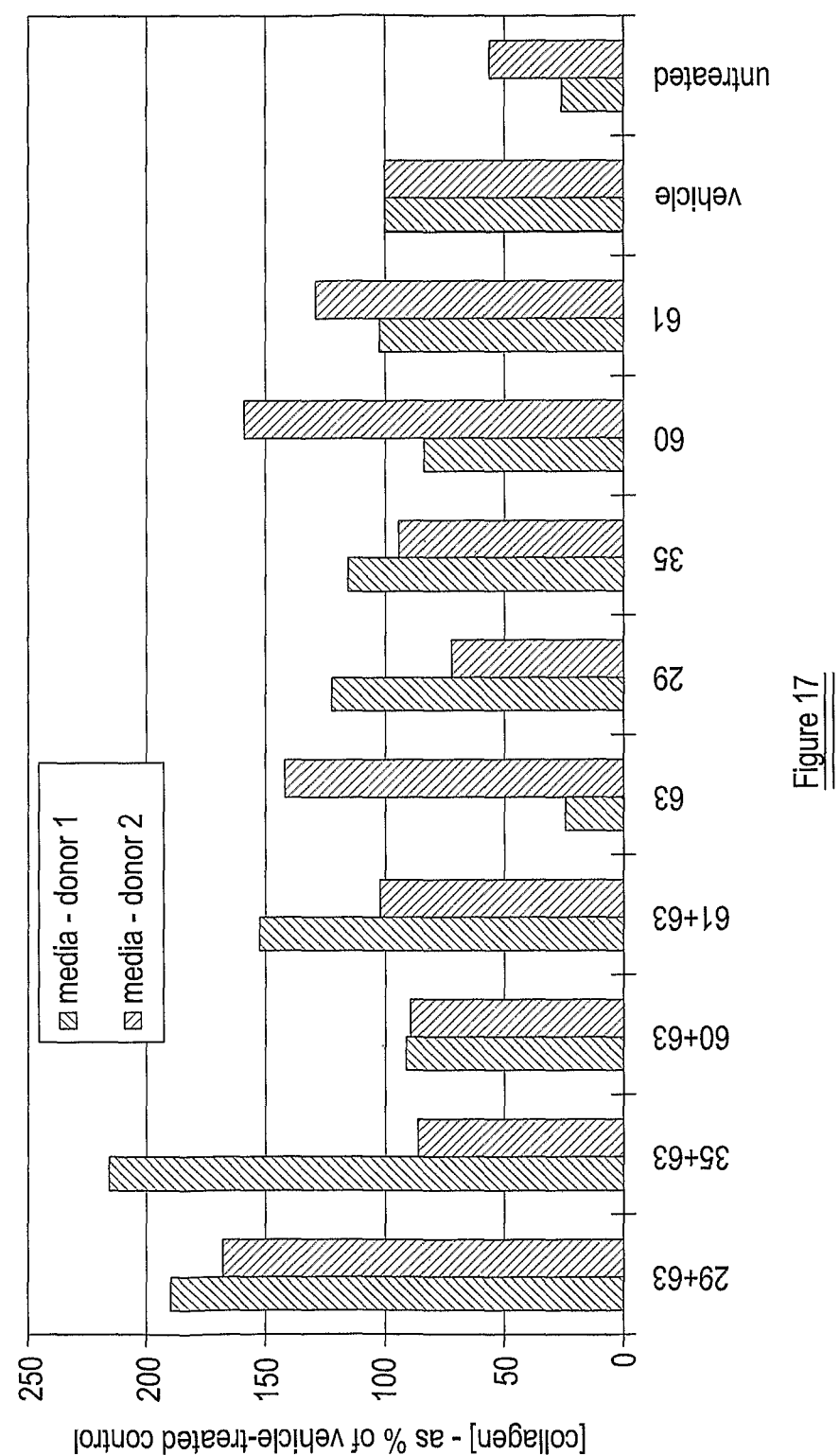
FIG. 17: Levels of secreted collagen I in the culture medium of human dermal fibroblasts treated with test oils/test oil combinations. Data shown are the means of values obtained from two separate cell culture wells. Oils are referred to on the x-axis by their reference number (See FIG. 16). The test oil combination of refined rosehip oil (Epi29) and *echium* oil (Epi63) resulted in the most consistent increase in collagen 1 in the culture medium. Raw data may be found in FIGS. 19 to 30.
Figure 18:
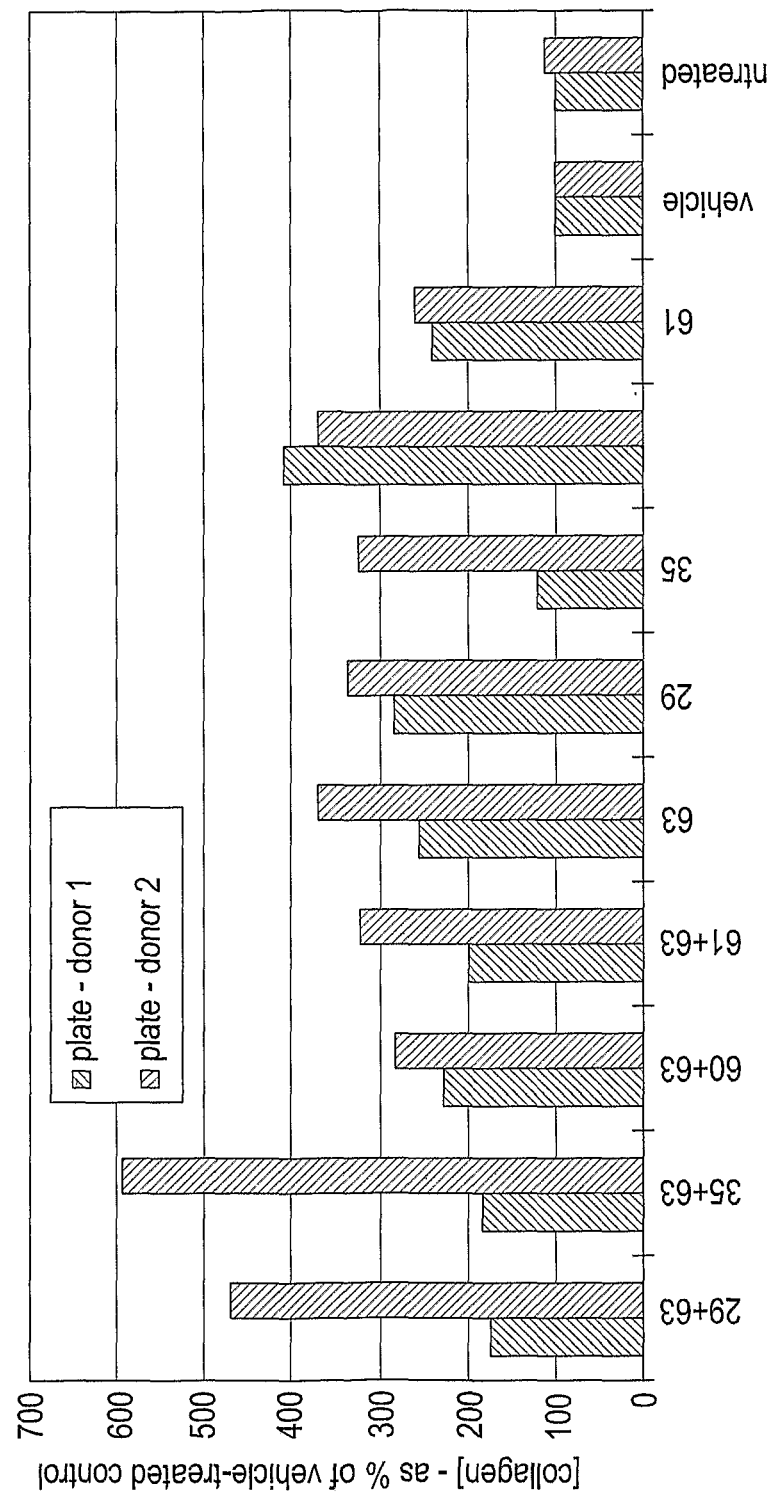
FIG. 18: Levels of secreted collagen I in the adhered to the wells of the culture plates, from human dermal fibroblasts treated with test oils/test oil combinations. Data shown are the means of values obtained from two separate cell culture wells. Oils are referred to on the x-axis by their reference number (See FIG. 16). All test oil combinations enhanced the levels of adhered collagen I in the cultures relative to vehicle-treated and untreated controls. With the exception of *jacaranda* oil (Epi60), the response of donor 2 cells to the test oils was greater than the response of donor 1 cells. Raw data may be found in FIGS. 19 to 30.
Figures 19, 20:
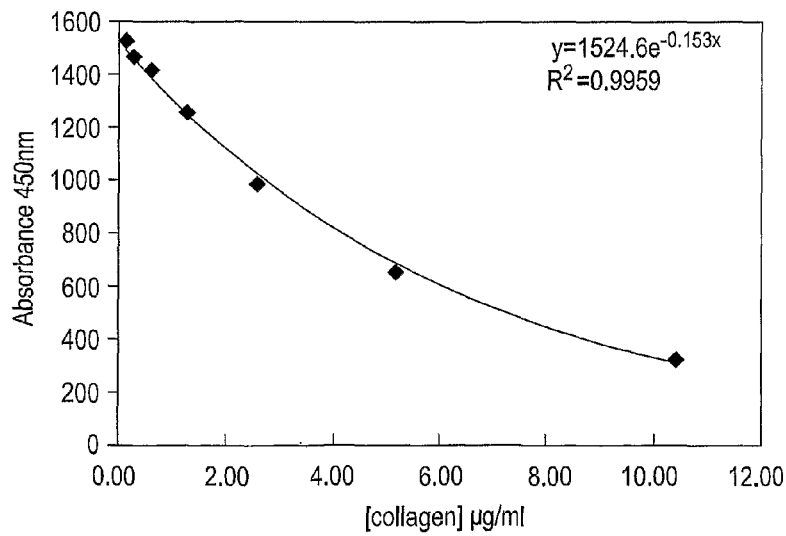
FIG. 19: Donor 1—plate layout and raw absorbance data for media samples. Samples with the same label in adjacent columns are replicate samples from the same culture well. Samples with same label in the same column are from different culture wells. Absorbance was determined at 450 nm.
FIG. 20: Donor 1—standard curve for media samples.
Figure 23:
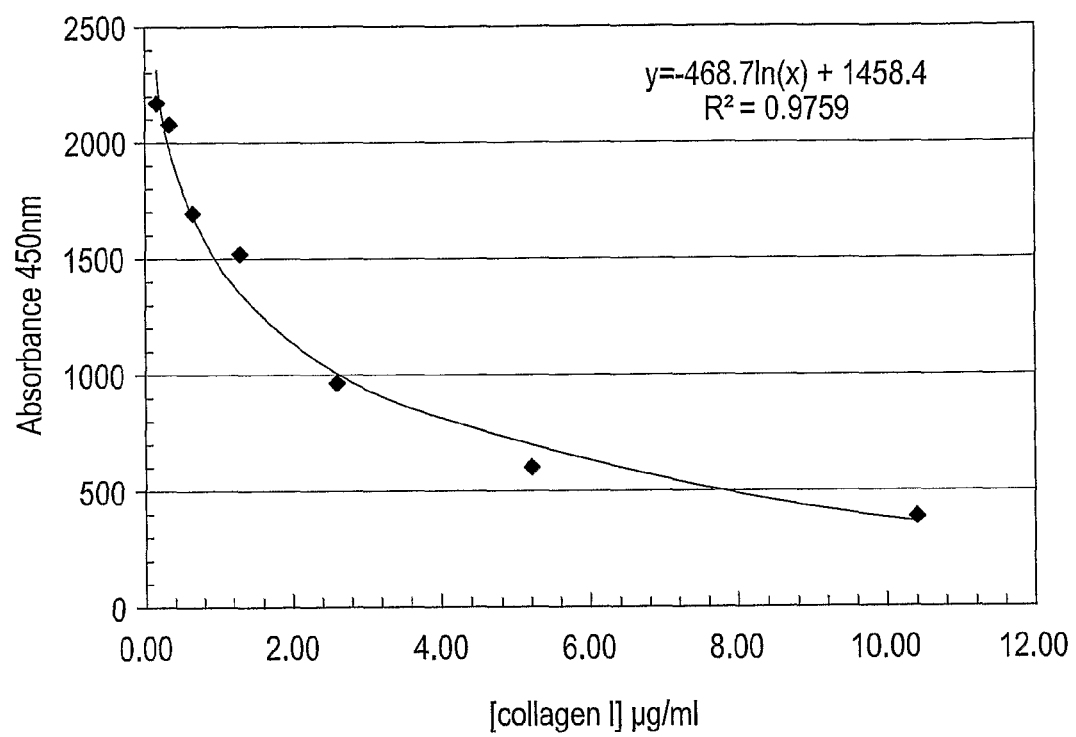
FIG. 23: Donor 1—standard curve for plate (adhered collagen) samples.
Figure 26:
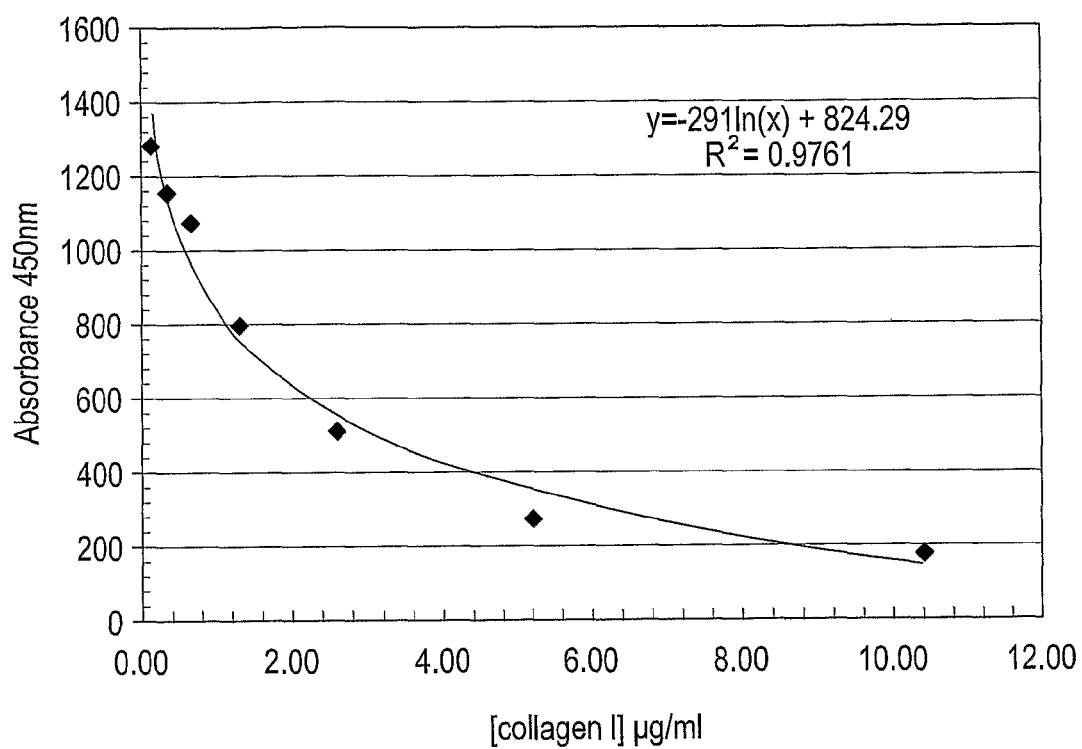
FIG. 26: Donor 2—standard curve for media samples.
Figure 29:
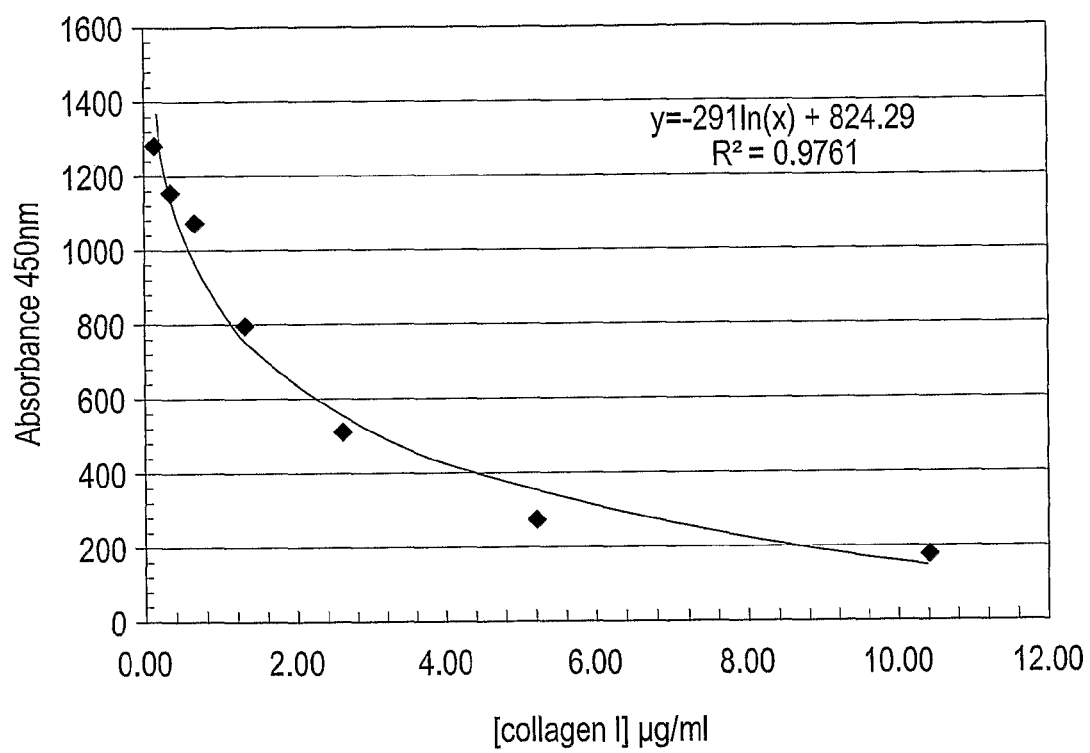
FIG. 29: Donor 2—standard curve for plate (adhered collagen) samples.

Dermal Fibroblast Cultures, Established from Skin Derived from Two Different Donors, Demonstrated Increased Levels of Secreted Collagen I Following Treatment with Test Oils Dermal fibroblast cultures derived from both donor 1 and donor 2 demonstrated increased levels of secreted collagen I following treatment with test oils. There was some donor variation in the magnitude of the response to each treatment, and in the treatments that demonstrated the greatest efficacy (particularly for the levels of measurable collagen in the culture medium). Such variation in the biological responses of cells derived from different skin donors is to be expected. The most consistent feature was that all oils/oil combinations increased the levels of adhered collagen I in the culture wells, relative to both vehicle-treated and untreated controls. Data for the levels of collagen in the media compartment and the adhered collagen compartment are shown in FIGS. 17 and 18.

Conclusions

The effect of test oils in increasing the levels of secreted collagen I in cultures of dermal fibroblasts has been confirmed.

Example 3

Preliminary Report on a Study to Further Establish the Roles of CODTA's when Combined with SDA in Collagen Production in Human Skin This example provides outline results of the effect of two test active ingredient mixes on collagen I secretion by human dermal fibroblasts. Human dermal fibroblasts (originally derived from explant cultures of normal human breast dermis) were cultured under standard conditions. Two test combinations of actives (CODTA's when combined with SDA) were initially screened for cytotoxicity before testing.

Collagen I levels were determined and are expressed as a percentage of the levels observed in samples from cultures treated with diluent (vehicle) alone.

Pepsin digests of both cell culture medium, and the cell culture surface (plate) from each treated culture well were analysed.

Jacaric Acid in combination with the Stearidonic Acid base was found to strongly induce collagen I secretion by human dermal fibroblasts under the culture conditions employed. Percentage increase 278%

Calendic Acid had similar potency to Jacaric Acid although its efficacy at increasing collagen I secretion was not so evident. Percentage increase 187%

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A composition for topical application to the skin of an animal comprising *echium* oil containing stearidonic acid in combination with one or more plant lipids containing octadecatrienoic acids, wherein the one or more plant lipids are selected from the group consisting of *jacaranda* oil (*Jacaranda mimosifolia*) and *calendula* oil (*Calendula officinalis*), wherein the composition is effective to increase collagen I production in skin, and wherein the ratio of *echium* oil to *jacaranda* oil and/or *calendula* oil is about 3:1.

2. The composition of claim 1, wherein the *echium* oil is extracted from *Echium plantaqineum L.*

3. The composition of claim 1 wherein the octadecatrienoic acid is Calendic acid and/or Jacaric acid.

4. The composition of claim 1, wherein the *echium* oil and one or more plant lipids are extracted from plant seed using a supercritical carbon dioxide extraction process.

5. A pharmaceutical composition comprising a composition according to claim 1 and a pharmaceutically acceptable excipient.

6. A method of treating skin comprising topically applying a composition or a pharmaceutical composition according to claim 1 to the skin.

7. A composition or a pharmaceutical composition according to claim 1 for topical application to the skin for use as a medicament for increasing collagen production in skin.

8. A composition for topical application to the skin of an animal comprising *echium* oil containing stearidonic acid in combination with one or more plant lipids containing octadecatrienoic acids selected from calendic and jacaric acid, wherein the one or more plant lipids are selected from the group consisting of *jacaranda* oil (*Jacaranda mimosifolia*) and *calendula* oil (*Calendula officinalis*), wherein the composition is effective to increase collagen I production in skin, and wherein the ratio of *echium* oil to *jacaranda* oil and/or *calendula* oil is about 3:1.

* * * * *